(12) United States Patent
Hazen et al.

(10) Patent No.: US 10,241,093 B2
(45) Date of Patent: *Mar. 26, 2019

(54) TRIMETHYLAMINE-CONTAINING COMPOUNDS FOR DIAGNOSIS AND PREDICTION OF DISEASE

(75) Inventors: Stanley L. Hazen, Pepper Pike, OH (US); Zeneng Wang, Shaker Heights, OH (US); Bruce S. Levison, Twinsburg, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/304,806

(22) Filed: Nov. 28, 2011

(65) Prior Publication Data

US 2012/0157397 A1    Jun. 21, 2012

Related U.S. Application Data

(63) Continuation-in-part of application No. PCT/US2010/036705, filed on May 28, 2010.

(60) Provisional application No. 61/181,858, filed on May 28, 2009.

(30) Foreign Application Priority Data

May 28, 2010    (WO) ................ PCT/US2010/036705

(51) Int. Cl.
| | | |
|---|---|---|
| *G01N 33/68* | (2006.01) | |
| *G01N 30/88* | (2006.01) | |
| *C12Q 1/02* | (2006.01) | |
| *C12Q 1/18* | (2006.01) | |
| *A61K 31/4164* | (2006.01) | |
| *A61K 31/43* | (2006.01) | |
| *A61K 31/496* | (2006.01) | |
| *A61K 31/7036* | (2006.01) | |
| *G01N 30/72* | (2006.01) | |

(52) U.S. Cl.
CPC ......... *G01N 30/88* (2013.01); *A61K 31/4164* (2013.01); *A61K 31/43* (2013.01); *A61K 31/496* (2013.01); *A61K 31/7036* (2013.01); *C12Q 1/025* (2013.01); *C12Q 1/18* (2013.01); *G01N 33/6893* (2013.01); *G01N 30/7233* (2013.01); *G01N 2030/8813* (2013.01); *G01N 2030/8822* (2013.01); *G01N 2800/04* (2013.01); *G01N 2800/042* (2013.01); *G01N 2800/044* (2013.01); *G01N 2800/32* (2013.01); *G01N 2800/323* (2013.01); *G01N 2800/50* (2013.01); *G01N 2800/52* (2013.01)

(58) Field of Classification Search
CPC ... G01N 2560/00; G01N 2800/00–2800/7095; G01N 33/48–33/567; G01N 33/68–33/6851

See application file for complete search history.

(56) References Cited

U.S. PATENT DOCUMENTS

| | | | |
|---|---|---|---|
| 6,040,147 A | 3/2000 | Ridker et al. | |
| 2001/0041741 A1* | 11/2001 | Sole et al. | ............... 514/561 |
| 2002/0173020 A1 | 11/2002 | Meyers et al. | |
| 2005/0106104 A1 | 5/2005 | Rosenberg | |
| 2005/0169901 A1* | 8/2005 | Pang et al. | .............. 424/93.45 |
| 2011/0189149 A1* | 8/2011 | Burcelin et al. | ......... 424/93.45 |

FOREIGN PATENT DOCUMENTS

| | | |
|---|---|---|
| CA | 2691147 | 3/2008 |
| WO | 2009073839 A1 | 6/2009 |

OTHER PUBLICATIONS

Pierpont, M.E.M., Judd, D., Goldenberg, I.F., Steves Ring, W., Olivari, M.T., Pierpont, G.L. (1989) Myocardial Carnitine in End-Stage Congestive Heart Failure. American Journal of Cardiology, vol. 64, p. 56-60.*
Seim, H., Eichler, K., Kleber, H.-P. (2001) "L(−)-Carnitine and its Precursor, γ-Butyrobetaine" from Nutraceuticals in Health and Disease Prevention, p. 217-256. Edited by Klaus Kramer. Published by Marcel Dekker.*
Bremer, J. (1983) Carnitine—Metabolism and Functions. Physiological Reviews, vol. 63, No. 4, p. 1420-1478.*
Vaz, F.M., Wanders, R.J.A. (2002) Carnitine biosynthesis in mammals. Biochemical Journal, vol. 361, p. 417-429.*
Wikoff, W.R., Gangoiti, J.A., Barshop, B.A., Siuzdak, G. (2007) Metabolomics Identifies Perturbations in Human Disorders of Propionate Metabolism. Clinical Chemistry, vol. 53, No. 12, p. 2169-2176.*
"Types of cardiovascular disease" from the World Health Organization. Retrieved on Dec. 28, 2015 [online]. Retrieved from <http://www.who.int/cardiovascular_diseases/en/cvd_atlas_01_types.pdf>.*
Koeth, R.A., Levison, B.S., Culley, M.K., Buffa, J.A., Wang, Z., Gregory, J.C., Org, E., Wu, Y., Li, L., Smith, J.D., Wilson Tang, W.H., DiDonato, J.A., Lusis, A.J., Hazen, S.L. (2014) Gamma-Butyrobetaine is a Proatherogenic Intermediate in gut Microbial Metabolism of L-Carnitine to TMAO. Cell Metabolism, vol. 20, p. 799-812.*
"Cardiovascular disease risk factors" from the World Heart Federation. Retrieved on Dec. 28, 2015 [online]. Retrieved from <http://www.world-heart-federation.org/cardiovascular-health/cardiovascular-disease-risk-factors/>.*
Koeth, R.A. et al. (2013) Intestinal microbiota metabolism of L-carnitine, a nutrient in red meat, promotes atherosclerosis. Nature Medicine, vol. 19, No. 5, p. 576-585.*
"Carnitine" from NIH Office of Dietary Supplements. Retrieved on Dec. 28, 2015 [online]. Retrieved from <https://ods.od.nih.gov/factsheets/Carnitine-HealthProfessional/?print=1>.*

(Continued)

*Primary Examiner* — Leigh C Maier
(74) *Attorney, Agent, or Firm* — Casimir Jones, S.C.; Jason R. Bond

(57) ABSTRACT

The present invention provides markers and methods for determining whether a subject, particularly a human subject, has or is at risk of developing, a disease such as cardiovascular disease, diabetes mellitus, insulin resistance, metabolic syndrome, NAFLD (Nonalcoholic Fatty Liver Disease) or NASH (Nonalcoholic Steatohepatitis) (e.g., within the ensuing year, two years, and/or three years). The present application also relates to the use of such markers and methods for monitoring the status of such diseases in a subject or the effects of therapeutic agents on subjects with such diseases.

4 Claims, 19 Drawing Sheets

(56) References Cited

OTHER PUBLICATIONS

Skagen, K. et al. (2016) The Carnitine-butyrobetaine-trimethylamine-N-oxide pathway and its association with cardiovascular mortality in patients with carotid atherosclerosis. Atherosclerosis, vol. 247, p. 64-69.*

Sessa, M. et al "Criteria for evaluation of novel markers . . . " Circulation (2009) vol. 119, pp. 2408-24016.*

Velasquez, M. et al "Trimethylamine N-oxide: the good, the bad . . . " Toxins (2016) vo 8, pp. 1-11.*

Sessa, R. et al "Chlamydia pneumoniae and atherosclerosis . . . " Int. J. Immunopathol. Pharamacol. (2009) vol. 22, No. 1, pp. 9-14.*

Tang, W. et al "Intestinal microbial metabolism . . . " NEJM (2013) vol. 368, No. 17, pp. 1575-1584.*

Visokinskas, A. et al "Use of mildronate in geriatric patients . . . " J. Ind. Acad. Geriat., vol. 3, pp. 110-113. (Year: 2005).*

Sjakste, N. et al "Mildronate: an antiischemic drug with multiple indications" Pharmacologyonline, vol. 1, pp. 1-18. (Year: 2006).*

Inoue, F. et al "Effect of sports activity on carnitine metabolism . . . " J. Chromatog. B, vol. 731, pp. 83-88. (Year: 1999).*

Moder, M. et al "Determination of urinary acylcarnitines . . . " J. Mass Specdtrom., vo 32, pp. 1195-1204, (Year: 1997).*

El-Aroussy et al. "Plasma carnitine levels as a marker of impaired left ventricular functions," Mol Cell Biochem., 213 (1-2):37-41, 2000.

Stenmark et al. "Crystal structure of CaiB, a type-III CoA transferase in carnitine metabolism," Biochemistry, 43 (44):13996-4003, 2004.

International Search Report and Written Opinion for Int'l Application No. PCT/US2010/036705, dated Sep. 30, 2010.

Bennett et al., "Trimethylamine-N-Oxide, a Metabolite Associated with Atherosclerosis, Exhibits Complex Genetic and Dietary Regulation," Cell Metabol., 2013, 17:49-60.

Mayr, "Recent Highlights of Metabolomics in Cardiovascular Research," Circ Cardiovasc Genet, 2011, 4:463-464.

International Search Report and Written Opinion, dated Mar. 27, 2013, for International Patent Application PCT/US2012/066731, 16 pages.

Vaz et al., Analysis of carnitine biosynthesis metabolites in urine by HPLC-electrospray tandem mass spectrometry. Clin Chem. Jun. 2002;48(6 Pt 1):826-34.

Wang et al., Analysis of acetylcholine, choline and butyrobetaine in human liver tissues by hydrophilic interaction liquid chromatography-tandem mass spectrometry. J Pharm Biomed Anal. Aug. 5, 2008;47(4-5):870-5.

Ansaldi et al., Aerobic TMAO respiration in *Escherichia coli*. Mol Microbiol. Oct. 2007;66(2):484-94.

Stenberg et al., Trimethylamine oxide respiration of Alteromonas putrefaciens NCMB 1735: Na+-stimulated anaerobic transport in cells and membrane vesicles. Appl Environ Microbiol. May 1984;47(5):1090-5.

* cited by examiner

FIG. 7A
Kaplan Meier plots of Tertiles of Crotonobetaine
for Death, MI, Stroke and Revascularization
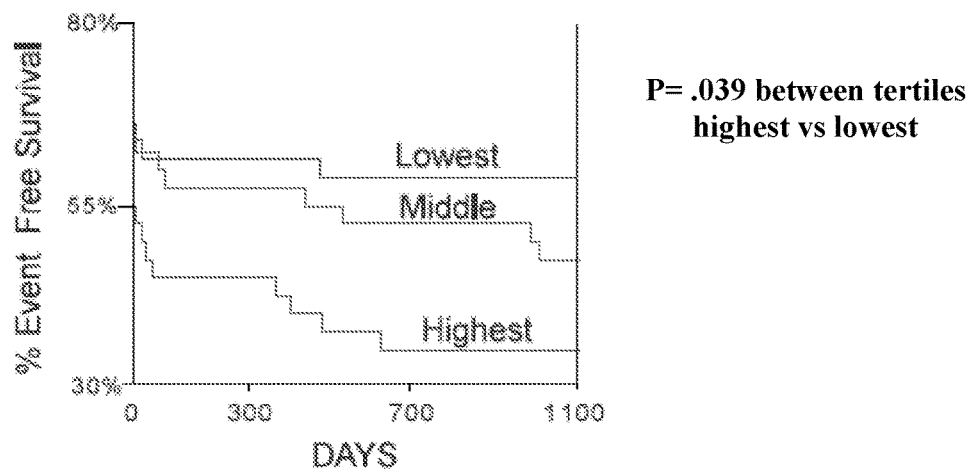
P= .039 between tertiles
highest vs lowest
Kaplan Meier plots of Tertiles of gamma-butyrobetaine
for Death, MI, Stroke and Revascularization
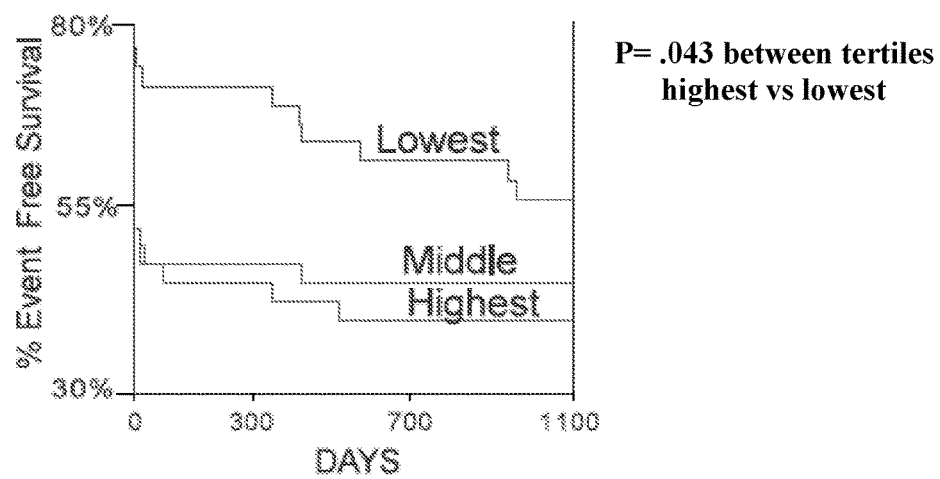
P= .043 between tertiles
highest vs lowest
FIG. 7B Kaplan Meier plots of Tertiles of Carnitine for Death, MI, Stroke and Revascularization P= .022 between tertiles highest vs lowest

D3-Carnitine

FIGURE 13

| Analyte | CAD | CHF |
|---|---|---|
| | Odds ratio (p value) | |
| Carnitine | 1.3 (<0.05) | 1.4 (<0.05) |
| Acetylcarnitine | 1.2 (<0.05) | 1.3 (<0.05) |
| Proprionylcarnitine | 1.3 (<0.05) | 1.1 (0.05) |
| Octanoylcarnitine | 1.7 (<0.05) | 1.3 (<0.05) |

TRIMETHYLAMINE-CONTAINING COMPOUNDS FOR DIAGNOSIS AND PREDICTION OF DISEASE

The present application is a Continuation-in-part of International Application PCT/US2010/036705 filed May 28, 2010, which claims priority to U.S. Provisional Application Ser. No. 61/181,858, filed May 28, 2009, both of which are herein incorporated by reference in their entireties.

FIELD OF THE INVENTION

The present invention relates to markers and methods for determining whether a subject, particularly a human subject, has or is at risk of developing, a disease or disorder such as cardiovascular disease, diabetes mellitus, insulin resistance, metabolic syndrome, NAFLD, or NASH (e.g., within the ensuing year, two years; and/or three years). The present application also relates to the use of such markers and methods for monitoring the status of such diseases and disorders in a subject or the effects of therapeutic agents on subjects with such diseases and disorders.

BACKGROUND

Cardiovascular disease (CVD) accounts for one in every two deaths in the United States and is the number one killer disease in the United States and most European countries. Thus, prevention of cardiovascular disease is an area of major public health importance. A low-fat diet and exercise are recommended to prevent CVD. In addition, a number of therapeutic agents may be prescribed by medical professionals to those individuals who are known to be at risk having CVD. More aggressive therapy, such as administration of multiple medications or surgical intervention may be used in those individuals who are at high risk of having CVD. Since CVD therapies may have adverse side effects, it is desirable to have methods for identifying those individuals who are at risk, particularly those individuals who are at high risk of experiencing an adverse cardiovascular event near term.

Currently, several risk factors are used by medical professionals to assess an individual's risk of developing or having CVD and to identify individuals at high risk. Major risk factors for cardiovascular disease include age, hypertension, family history of premature CVD, smoking, high total cholesterol, high LDL cholesterol, low HDL cholesterol, obesity and diabetes. The major risk factors for CVD are additive, and are typically used together by physicians in a risk prediction algorithm to target those individuals who are most likely to benefit from treatment for CVD. These algorithms achieve a high sensitivity and specificity for predicting risk of CVD within 10 years. However, the ability of the present algorithms to predict a higher probability of developing CVD is limited. Among apparently healthy adults with none of the current risk factors, the 10-year risk for developing CVD is still considerable, and is approximately 2% or higher, depending upon age. In addition, a large number of CVD complications occur in individuals with apparently low to moderate risk profiles, as determined using currently known risk factors. Thus, there is a need to expand the present cardiovascular risk algorithm to identify a larger spectrum of individuals at risk for or affected with CVD.

A significant factor in the development of cardiovascular disease is the presence of atherosclerosis. However, the mechanism of atherosclerosis is not well understood. Over the past decade a wealth of clinical, pathological, biochemical and genetic data support the notion that atherosclerosis is a chronic inflammatory disorder. Acute phase reactants (e.g. C-reactive protein, complement proteins), sensitive but non-specific markers of inflammation, are enriched in fatty streaks and later stages of atherosclerotic lesions. In a recent prospective clinical trial, base-line plasma levels of C-reactive protein independently predicted risk of first-time myocardial infarction and stroke in apparently healthy individuals. U.S. Pat. No. 6,040,147 describes methods which use C-reactive protein, cytokines, and cellular adhesion molecules to characterize an individual's risk of developing a cardiovascular disorder. Although useful, these markers may be found in the blood of individuals with inflammation due to causes other than CVD, and thus, these markers may not be specific enough. Moreover, modulation of their levels has not been established to reproducibly predict a decrease in the morbidity or mortality of CVD. Accordingly, there exists a need for additional markers for assessing a subject's risk of CVD.

SUMMARY OF THE INVENTION

The present invention provides markers and methods for determining whether a subject, particularly a human subject, has or is at risk of developing, a disease or disorder such as cardiovascular disease, diabetes mellitus, insulin resistance, metabolic syndrome, NAFLD (Nonalcoholic Fatty Liver Disease) or NASH (Nonalcoholic Steatohepatitis) (e.g., within the ensuing year, two years, and/or three years). The present application also relates to the use of such markers and methods for monitoring the status of such diseases in a subject or the effects of therapeutic agents or interventions on subjects with such diseases.

In some embodiments, the present invention provides methods of identifying a subject at risk of experiencing a complication of atherosclerotic cardiovascular disease, comprising: a) determining levels of a trimethylamine (TMA)-containing compound (e.g., using an analytic device) in a biological sample obtained from the subject, wherein the choline-related TMA-containing compound is selected from choline, crotonobetaine (both the cis and trans isomers), gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, and phosphatidylcholine; and b) comparing levels of the choline-related TMA-containing compound in the biological sample to a control value; wherein a subject whose levels of the choline-related TMA-containing compound in the biological sample are elevated as compared to the control value is at risk of experiencing a complication of atherosclerotic cardiovascular disease.

In certain embodiments, the methods further comprise the step of characterizing the subject's risk of experiencing a complication of atherosclerotic cardiovascular disease as higher if levels of the TMA-containing compound are higher than the control value, and lower if the levels of the TMA-containing compound are lower than the control value. In other embodiments, the complication is one or more of the following: non-fatal myocardial infarction, stroke, transient ischemic attack, angina pectoris, transient ischemic attacks, peripheral artery disease, congestive heart failure, cardiomyopathy (ischemic and non-ischemic), aortic aneurysm, aortic dissection, need for revascularization (coronary artery bypass grafting, coronary angioplasty, coronary stenting) and death. In further embodiments, the risk is a risk of experiencing a complication of atherosclerotic cardiovascular disease over the long term, such as within the ensuing three years or longer time points (e.g., four years, five years, six year, seven years, or longer).

In some embodiments, the present invention provides methods of characterizing a subject's risk of having or developing cardiovascular disease, comprising: a) determining levels of a choline-related trimethylamine (TMA)-containing compound using an analytic device in a biological sample obtained from the subject, wherein the choline-related TMA-containing compound is selected from choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, and phosphatidylcholine; and b) comparing levels of the choline-related TMA-containing compound in the biological sample to a control value; wherein a subject whose levels of the choline-related TMA-containing compound in the biological sample are elevated as compared to the control value is at risk of having or developing cardiovascular disease.

In some embodiments, the methods further comprise treating the subject with a therapeutic that reduces the symptoms of cardiovascular disease or that reduces the risk of cardiovascular disease. In certain embodiments, the therapeutic is selected from the group consisting of: an antibiotic, a probiotic, an alpha-adrenergic blocking drug, an angiotensin-converting enzyme inhibitor, an antiarrhythmic drug, an anticoagulant, an antiplatelet drug, a thromybolytic drug, a beta-adrenergic blocking drug, a calcium channel blocker, a brain acting drug, a cholesterol-lowering drug, a digitalis drug, a diuretic, a nitrate, a peripheral adrenergic antagonist, and a vasodilator.

In certain embodiments, the methods, the methods further comprise the step of characterizing the subject's risk of having or developing cardiovascular disease as higher if levels of the choline-related TMA-containing compound are higher than the control value, and lower if the levels of the choline-related TMA-containing compound are lower than the control value. In other embodiments, the risk is a risk of having or developing cardiovascular disease over the long term, such as within the ensuing three years or longer time points.

In additional embodiments, the present invention provides methods of evaluating the efficacy of a cardiovascular disease therapeutic agent or intervention (e.g., use of a device, or a dietary prescription, or an exercise program) in a subject with cardiovascular disease, comprising: a) determining levels of a choline-related trimethylamine (TMA)-containing compound using an analytic device in a biological sample obtained from the subject during or after administration of the therapeutic agent, wherein the choline-related TMA-containing compound is selected from choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, and phosphatidylcholine; and b) comparing levels of the choline-related TMA-containing compound in the biological sample to a predetermined value; c) determining the therapeutic agent or intervention to be efficacious if levels of the choline-related TMA-containing compound are lower than the predetermined value.

In some embodiments, the present invention provides methods of identifying a subject as having or at risk of developing: diabetes mellitus, insulin resistance, metabolic syndrome, NAFLD, or NASH, comprising: a) determining levels of a choline-related trimethylamine (TMA)-containing compound using an analytic device in a biological sample obtained from the subject; and b) comparing levels of the choline-related TMA-containing compound in the biological sample to a control value; wherein a subject whose levels of the choline-related TMA-containing compound in the biological sample are elevated as compared to the control value is at risk of developing, or has: diabetes mellitus, insulin resistance, metabolic syndrome, NAFLD, or NASH.

In additional embodiments, the methods further comprise the step of characterizing the subject's risk of having or developing diabetes mellitus, insulin resistance, metabolic syndrome, NAFLD, or NASH as higher if levels of the choline-related TMA-containing compound are higher than the control value, and lower if the levels of the choline-related TMA-containing compound are lower than the control value. In other embodiments, the choline-related TMA-containing compound is selected from the group consisting of: choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, and phosphatidylcholine. In further embodiments, the choline-related TMA-containing compound is selected from the group consisting of: trimethylamine-N-oxide, choline, or betaine. In other embodiments, the risk is a risk of developing diabetes mellitus, insulin resistance, metabolic syndrome, NAFLD, or NASH within the ensuing three years.

In some embodiments, the present invention provides methods of evaluating the efficacy of a therapeutic agent or intervention in a subject with a disease selected from: diabetes mellitus, insulin resistance, metabolic syndrome, NAFLD, or NASH, comprising: a) determining levels of a choline-related trimethylamine (TMA)-containing compound using an analytic device in a biological sample obtained from the subject during or after administration of the therapeutic agent; b) comparing levels of the choline-related TMA-containing compound in the biological sample to a predetermined value; and c) determining the therapeutic agent to be efficacious in treating diabetes mellitus, insulin resistance, metabolic syndrome, NAFLD, or NASH if levels of the choline-related TMA-containing compound are lower than the predetermined value.

In certain embodiments, the present invention provides methods of treating, or preventing the development of, a condition comprising; administering probiotics, prebiotics, and antibiotics to a subject such that the formation of trimethylamine, TMANO, crotonobetaine, and/or gamma-butyrotetaine (or short chain carnitines (e.g., iC2, C3, and C4), from carnitine in the subject is reduced thereby at least partially treating, or preventing the development of, a condition selected from the group consisting of: cardiovascular disease, diabetes mellitus, insulin resistance, metabolic syndrome, NAFLD, or NASH. In particular embodiments, the antibiotics are administered to the subject over a short course of time such as seven days or less (e.g., 7, 6, 5, 4, 3, 2, or 1 day). In certain embodiments, the antibiotic is one antibiotic or a combination of antibiotics selected from the group consisting of: metronidazole, ciprofloxacin, neomycin, amoxicillin, amoxicilling/clavulinic acid, chloramphenicol, or an antibiotic in the class of a cephalosporin, a macrolide, beta lactams, aminoglycosides, tretracyclins, quinolones, sulfonamindes or sulfones. In further embodiments, the subject does not have trimethylaminuria.

In particular embodiments, the present invention provides methods of treating, or preventing the development of, a condition comprising; administering antibiotics to a subject such that the formation of trimethylamine, TMANO, crotonobetaine, and/or gamma-butyrotetaine (or other choline-related TMA-containing compound) from carnitine in the subject is reduced thereby at least partially treating, or preventing the development of, a condition selected from the group consisting of: cardiovascular disease, diabetes mellitus, insulin resistance, metabolic syndrome, NAFLD, or NASH.

In some embodiments, the present invention provides methods of screening a candidate inhibitor comprising: a) combining: i) a choline-related trimethylamine (TMA)-containing compound, ii) intestinal microflora capable of cleaving the choline-related TMA-containing compound to form trimethylamine, and iii) a candidate inhibitor; and b) determining the ability of the candidate inhibitor to inhibit the formation of the trimethylamine by detecting the level of the trimethylamine that is formed or the downstream metabolite trimethylamine oxide that is formed, crotonobetaine that is formed, or gammabutyrobetaine that is formed.

In certain embodiments, the choline-related TMA-containing compound is selected from the group consisting of: choline, carnitine, betaine, phosphocholine, phosphatidylcholine, glycerophosphocholine, crotonobetaine, 4-Trimethylammoniumbutyraldehyde, dehydrocarnifine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and gamma-butyrobetaine. In other embodiments, the intestinal microflora is obtained from a intestinal lavage material, a specific section of intestine, cecum homogenate, cecum washes, or stool. In further embodiments, the detecting the level of the trimethylamine that is formed is performed by mass spectrometry or HPLC. In additional embodiments, the choline-related TMA-containing compound is detectably labeled (e.g., with a chromophore or fluorescent moiety). In some embodiments, the candidate inhibitor comprises an antibiotic.

In some embodiments, the present invention provides methods of treating, or preventing the development of, a condition comprising; administering an inhibitor to a subject such that the formation of trimethylamine, TMANO, crotonobetaine, and/or gamma-butyrotetaine from carnitine in the subject is reduced thereby at least partially treating, or preventing the development of, a condition selected from the group consisting of: cardiovascular disease, diabetes mellitus, insulin resistance, metabolic syndrome, NAFLD, or NASH. In certain embodiments, the TMA formation inhibitor is selected from the group consisting of: neomycin, amoxicillin, metronidazole, activated charcoal, or copper chlorophyllin, amoxicilling/clavulinic acid, chloramphenicol, or an antibiotic in the class of a cephalosporin, a macrolide, beta lactams, aminoglycosides, tretracyclins, quinolones, sulfonamindes or sulfones.

In some embodiments, described herein are methods for identifying subjects with or likely to develop heart failure, cardiomyopathy (ischemic or non-ischemic), ventricular systolic dysfunction, diastolic dysfunction, aortic dissection, or aortic aneurysm. The methods involve measuring levels of choline-related trimethylamine-containing compounds in test samples from the subjects.

One aspect of the present invention provides a method of identifying a subject at risk of experiencing heart failure, cardiomyopathy (ischemic or non-ischemic), ventricular systolic dysfunction, diastolic dysfunction, aortic dissection, or aortic aneurysm within the ensuing three years that includes determining levels of a choline-related trimethylamine-containing compound using an analytic device in a biological sample obtained from the subject; comparing levels of the choline-related trimethylamine-containing compound in the biological sample to a control value; and characterizing the subject's risk of experiencing heart failure, aortic dissection, or aortic aneurysm within the ensuing three years as higher if levels of the choline-related trimethylamine-containing compound are higher than the control value, and lower if levels of the choline-related trimethylamine-containing compound are lower than the control value.

Another aspect of the invention provides a method of diagnosing a subject with heart failure cardiomyopathy (ischemic or non-ischemic), ventricular systolic dysfunction, diastolic dysfunction, that includes determining levels of a choline-related trimethylamine-containing compound using an analytic device in a biological sample obtained from the subject; comparing levels of the choline-related trimethylamine-containing compound in the biological sample to a control value; and diagnosing the subject as being more likely to have heart failure if levels of the choline-related trimethylamine-containing compound are higher than the control value.

Yet another aspect of the invention provides a method of diagnosing a subject with an aortic disorder that includes determining levels of a choline-related trimethylamine-containing compound using an analytic device in a biological sample obtained from the subject; comparing levels of the choline-related trimethylamine-containing compound in the biological sample to a control value; and diagnosing the subject as being more likely to have an aortic disorder if levels of the choline-related trimethylamine-containing compound are higher than the control value. In some embodiments of the invention the aortic disorder is an aortic dissection, whereas in other embodiments the aortic disorder is an aortic aneurysm.

In certain embodiments of the invention, the choline-related trimethylamine-containing compound is trimethylamine-N-oxide, choline, betaine, crotonobetaine, gamma-butyrobetaine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, or carnitine. In one embodiment, the choline-related trimethylamine-containing compound is trimethylamine-N-oxide. In a further embodiment, the choline-related trimethylamine-containing compound is choline or betaine. In further embodiments of the method, a plurality of choline-related trimethylamine-containing compounds in the biological sample are determined.

In a further embodiments of the invention, the biological sample is whole blood, serum, plasma, exhaled breath, urine, cerebrospinal fluid, or bronchoalveolar lavage, while in further embodiments the biological sample is blood, serum or plasma. In yet another embodiment, the analytic device is a mass spectrometer. In some embodiments of the method, the subject does not have any signs or symptoms of cardiovascular disease. In certain embodiments, the exhaled breath is collected in a bag, sack, container or other collection device.

BRIEF DESCRIPTION OF THE FIGURES

FIG. 12A shows results from testing in plasma and FIG. 12B shows exhaled breath sample testing.

FIG. 13 shows results from Example 11 demonstrating that carnitine and various indicated acylcarnitines are associated with cardiac risk.

DETAILED DESCRIPTION OF THE INVENTION

Figure 1:
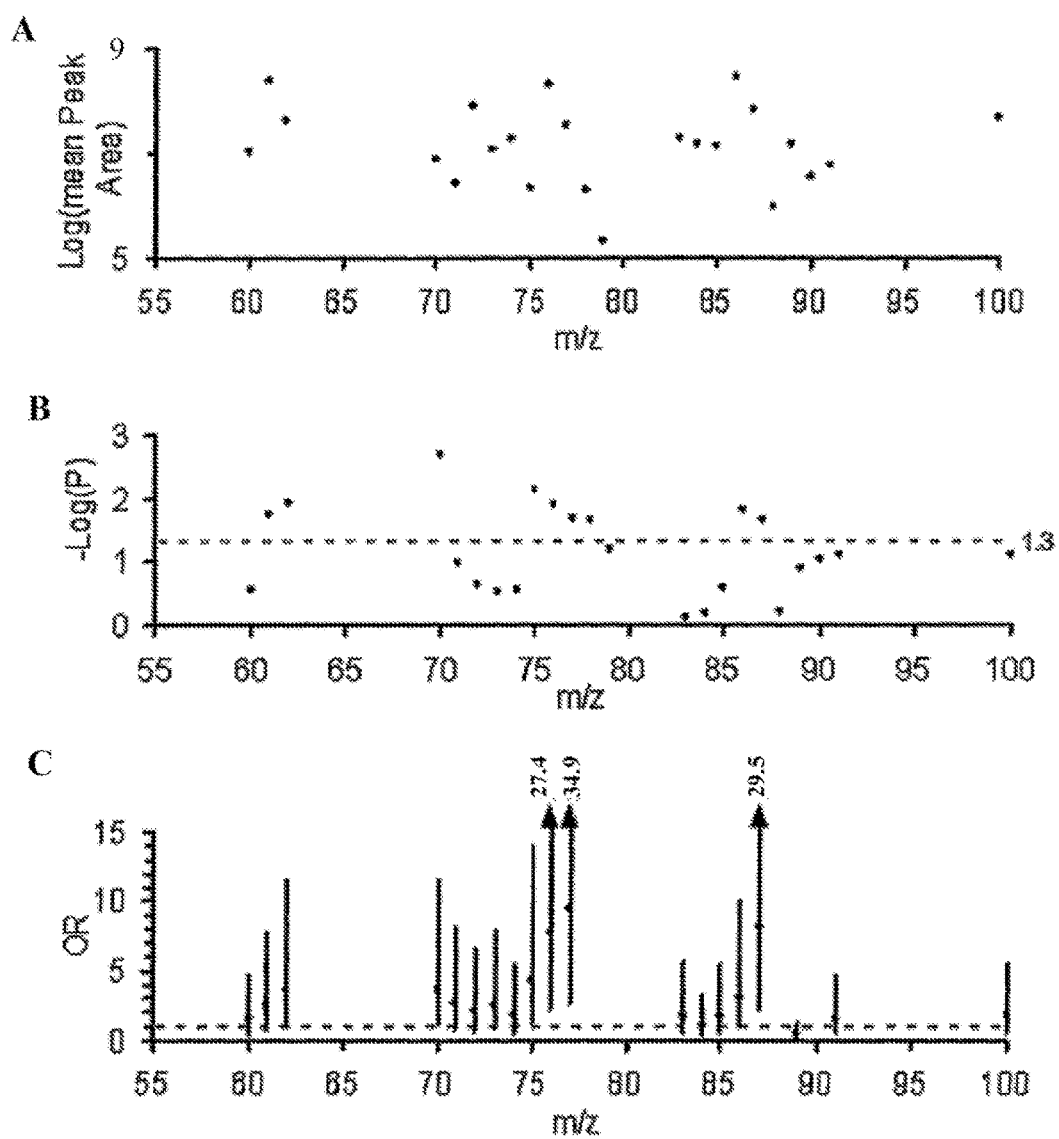
FIG. 1(a-c) provides graphs showing a peak area of extracted ion chromatograms in positive-ion MS1 mode at m/z ranging from 50 to 100. The component with m/z=76 was identified as TMANO (trimethylamine N-oxide) by reverse phase high performance liquid chromatography (HPLC) coupled to a mass spectrometer.

The present invention provides markers and methods for determining whether a subject, particularly a human subject, has or is at risk of developing, a disease such as cardiovascular disease, diabetes mellitus, insulin resistance, metabolic syndrome, NAFLD (Nonalcoholic Fatty Liver Disease) or NASH (Nonalcoholic Steatohepatitis) (e.g., within the ensuing year, two years, and/or three years, or longer). The present application also relates to the use of such markers and methods for monitoring the status of such diseases or disorders in a subject or the effects of therapeutic agents or interventions on subjects with such diseases.

In one embodiment, the present invention provides methods and markers for characterizing a subject's, particularly a human subject's, risk of having cardiovascular disease, particularly atherosclerotic cardiovascular disease. Examples of cardiovascular disease include heart failure, aortic dissection, and aortic aneurysms. In another embodiment, the present invention provides methods of characterizing a subject's risk of developing cardiovascular disease. In another embodiment, the present invention provides methods for characterizing a subject's risk of experiencing a cardiovascular (CVD) event within the ensuing year, 2 years, or 3 years. The present methods are useful for identifying those subjects who are in need of highly aggressive CVD therapies or interventions as well as those subjects who require no therapies or interventions targeted at inhibiting or preventing CVD or complications of CVD.

As used herein, the terms "cardiovascular disease" (CVD) or "cardiovascular disorder" are terms used to classify numerous conditions affecting the heart, heart valves, and vasculature (e.g., veins and arteries) of the body and encompasses diseases and conditions including, but not limited to arteriosclerosis, atherosclerosis, myocardial infarction, acute coronary syndrome, angina, congestive heart failure, aortic aneurysm, aortic dissection, iliac or femoral aneurysm, pulmonary embolism, primary hypertension, atrial fibrillation, stroke, transient ischemic attack, systolic dysfunction, diastolic dysfunction, myocarditis, atrial tachycardia, ventricular fibrillation, endocarditis, arteriopathy, vasculitis, atherosclerotic plaque, vulnerable plaque, acute coronary syndrome, acute ischemic attack, sudden cardiac death, peripheral vascular disease, coronary artery disease (CAD), peripheral artery disease (PAD), and cerebrovascular disease.

As used herein, the term "atherosclerotic cardiovascular disease" or "disorder" refers to a subset of cardiovascular disease that include atherosclerosis as a component or precursor to the particular type of cardiovascular disease and includes, without limitation, CAD, PAD, cerebrovascular disease. Atherosclerosis is a chronic inflammatory response that occurs in the walls of arterial blood vessels. It involves the formation of atheromatous plaques that can lead to narrowing ("stenosis") of the artery, and can eventually lead to partial or complete closure of the arterial opening and/or plaque ruptures. Thus atherosclerotic diseases or disorders include the consequences of atheromatous plaque formation and rupture including, without limitation, stenosis or narrowing of arteries, heart failure, aneurysm formation including aortic aneurysm, aortic dissection, and ischemic events such as myocardial infarction and stroke A cardiovascular event, as used herein, refers to the manifestation of an adverse condition in a subject brought on by cardiovascular disease, such as sudden cardiac death or acute coronary syndromes including, but not limited to, myocardial infarction, unstable angina, aneurysm, or stroke. The term "cardiovascular event" can be used interchangeably herein with the term cardiovascular complication. While a cardiovascular event can be an acute condition, it can also represent the worsening of a previously detected condition to a point where it represents a significant threat to the health of the subject, such as the enlargement of a previously known aneurysm or the increase of hypertension to life threatening levels.

As used herein, the term "diagnosis" can encompass determining the nature of disease in a subject, as well as determining the severity and probable outcome of disease or episode of disease and/or prospect of recovery (prognosis). "Diagnosis" can also encompass diagnosis in the context of rational therapy, in which the diagnosis guides therapy, including initial selection of therapy, modification of therapy (e.g., adjustment of dose and/or dosage regimen or lifestyle change recommendations), and the like.

The terms "individual," "host," "subject," and "patient" are used interchangeably herein, and generally refer to a mammal, including, but not limited to, primates, including simians and humans, equines (e.g., horses), canines (e.g., dogs), felines, various domesticated livestock (e.g., ungulates, such as swine, pigs, goats, sheep, and the like), as well as domesticated pets and animals maintained in zoos. In some embodiments, the subject is specifically a human subject.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and", and "the" include plural referents unless the context clearly dictates otherwise. Thus, for example, reference to "a sample" includes a plurality of such samples and reference to "a specific enzyme" (e.g., arginase) includes reference to one or more arginase polypeptides and equivalents thereof known to those skilled in the art, and so forth.

Unless otherwise indicated, all numbers expressing quantities of ingredients, properties such as molecular weight, reaction conditions, and so forth as used in the specification and claims are to be understood as being modified in all instances by the term "about." Accordingly, unless otherwise indicated, the numerical properties set forth in the following specification and claims are approximations that may vary depending on the desired properties sought to be obtained in embodiments of the present invention. Notwithstanding that the numerical ranges and parameters setting forth the broad scope of the invention are approximations, the numerical values set forth in the specific examples are reported as precisely as possible. Any numerical values; however, inherently contain certain errors necessarily resulting from error found in their respective measurements.

In one embodiment, the present methods include determining the levels of choline-related trimethylamine-containing compounds in a biological sample (e.g, a bodily fluid obtained from a subject). Choline-related trimethylamine-containing compounds include betaine, trimethylamine-N-oxide (TMANO), choline, acetylcholine, carbachol acetylcarnitine, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, and phosphatidylcholine. In an additional embodiment, the methods include determining the levels of one or more of the three compounds TMANO, choline, and betaine. In an additional embodiment, the present methods comprise determining the levels TMANO in a biological sample. In another embodiment, the methods comprise determining levels of choline, betaine, or both in a biological sample from the subject.

In certain embodiments, levels of trimethylamine-N-oxide (TMANO), choline, betaine, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, or any combination thereof in a biological sample from the subject are compared to a corresponding control value or values that are derived from measurements of TMANO, choline, betaine, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, or any combination thereof in comparable biological samples obtained from a reference cohort. Corresponding values, as used herein, refer to use of an appropriate control for a given compound, such as determining the reference population levels of TMANO to use as a control value for comparison to TMANO levels determined in a subject. Levels of TMANO, choline, betaine, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine (also called lecithin), or any combination thereof in a biological sample obtained from a subject, alternatively, may be compared to levels of an internal standard in the biological sample obtained from the subject. As is known to those skilled in the art, internal standards can be a variety of compounds, typically similar to the target analyte such as a heavy isotope labeled standard. Internal standards are a compound that can be added to a sample in a known amount and help quantify the analyte in a sample. For example, internal standards that can be used to quantify choline include heavy isotope labeled choline, or a structurally related compound such as acetyl-β-methylcholine and butyrylcholine. In certain embodiments, the biological sample is urine or blood, or a fluid derived from blood, e.g. serum or plasma, or exhaled breath.

In one embodiment, the comparison characterizes a subject's risk of having CVD, as determined using standard protocols for diagnosing CVD. Further embodiments are directed to characterizing the present risk of having atherosclerotic CVD. Moreover, the extent of the difference between the subject's TMANO, choline, crotonobetaine (cis and trans), gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine levels and the control value is also useful for characterizing the extent of the risk and thereby, determining which subjects would most greatly benefit from certain therapies or interventions. More specifically, there may be a positive correlation between the difference and the extent of the risk such that a large difference in levels corresponds to a large amount of risk.

In another embodiment, the comparison characterizes the subject's risk of developing CVD, diabetes mellitus, insulin resistance, metabolic syndrome, NAFLD, or NASH in the future. As illustrated in Example 2 herein, choline-related trimethylamine-containing compounds have prognostic utility for identifying the likelihood that a subject will develop CVD. While not intending to be bound by theory, there appears to be a link between choline metabolism, gut flora involved in choline metabolism, and the risk for developing CVD, diabetes mellitus, insulin resistance, metabolic syndrome, NAFLD, or NASH, and/or experiencing a significant cardiovascular event, and/or experiencing a significant complication of cardiovascular disease, diabetes mellitus, insulin resistance, metabolic syndrome, NAFLD, or NASH. Significant complications of diabetes mellitus, insulin resistance, metabolic syndrome include atherosclerotic heart disease, microvascular disease, retinopathy, nephropathy, neuropathy and dyslipidemia. Significant complications of NAFLD and/or NASH include hepatic cancer, cirrhosis, hepatic failure, hepatic encephalopathy.

For example, the comparison of the amount of choline-related trimethylamine-containing compounds in a subject to control values can be used to characterize the subject's risk of experiencing a cardiovascular event within the ensuing, three years, or in certain embodiments, two years, or in certain embodiments, one year (or any period therebetween). The present methods can also be used to determine if a subject presenting with chest pain is at risk of experiencing a cardiovascular event, such as a myocardial infarction, reinfarction, the need for revascularization, and/or death, near term. In this context, the term "near term" means within the following day, 3 months, 6 months, or year after the subject presents with chest pain.

Also provided herein are methods for monitoring over time the status of CVD, diabetes mellitus, insulin resistance, metabolic syndrome, NAFLD, or NASH, in a subject. Further embodiments are directed to monitoring over time the status of atherosclerotic CVD. In one embodiment, the method comprises determining the levels of TMANO, choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in a biological sample taken from the subject at an initial time and in a corresponding biological sample taken from the subject at a subsequent time. An increase in levels of TMANO, choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine and/or betaine in a biological sample taken at the subsequent time as compared to the initial time indicates that a subject's risk of having CVD, diabetes mellitus, insulin resistance, metabolic syndrome, NAFLD, or NASH has increased. A decrease in levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine indicates that the subject's risk of having CVD, diabetes mellitus, insulin resistance, metabolic syndrome, NAFLD, or NASH has decreased. For those subjects who have already experienced a cardiovascular event such as a myocardial infarction or ischemic stroke, such methods are also useful for assessing the subject's risk of experiencing a subsequent cardiovascular event. In such subjects, an increase in levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine indicates that the subject is at increased risk of experiencing a subsequent adverse cardiovascular event. A decrease in levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the subject over time indicates that the subject's risk of experiencing a subsequent adverse cardiovascular event has decreased.

The methods of the present invention can also be directed to detection, monitoring, or diagnosis of subjects with regard to specific cardiovascular diseases or cardiovascular events. For example, the methods of the invention can be directed to identifying subjects at risk of developing heart failure or aortic disorders such as aortic aneurysm or aortic dissection.

Heart failure is a form of cardiovascular disease is a condition in which a problem with the structure or function of the heart impairs its ability to supply sufficient blood flow to meet the body's needs, characterized by compromised ventricular systolic or diastolic functions, or both. Heart failure may be manifested by symptoms of poor tissue perfusion alone (e.g., fatigue, poor exercise tolerance, and/or confusion) or by both symptoms of poor tissue perfusion and congestion of vascular beds (e.g., dyspnea, decreased renal function, cardiorenal syndrome, pleural effusion, pulmonary edema, distended neck veins, congested liver, and/or peripheral edema). Congestive heart failure represents a form of heart failure where cardiac output is low, in contrast with high output cardiac failure, in which the body's requirements for oxygen and nutrients are increased, and demand outstrips what the heart can provide.

Heart failure can occur as a result of one or more causes. A major cause is secondary atherosclerotic disease, where one or more ischemic events such as a heart attack result in ischemic injury to the heart and decreased function. This type of heart failure is referred to as ischemic heart failure, because the cause of the cardiac dysfunction was secondary to the ischemic injury. Ischemic heart failure, also sometimes called ischemic cardiomyopathy, can also result from other cardiovascular conditions leading to ischemic injury, such as atherosclerosis that limits blood flow.

Heart failure can also occur as a result of causes other than ischemia, and such forms of heart failure are referred to as non-ischemic heart failure. Examples of non-ischemic heart failure include myocarditis resulting from viral infection, amyloidosis of cardiac tissue, arrhythmia, manifestation of genetic defects, injury from abuse of alcohol, drugs, or cigarettes, other sources of injury to cardiac tissue such as infection by bacteria or parasites, or vitamin deficiency.

Aortic dissection is a tear in the wall of the aorta that causes blood to flow between the layers of the wall of the aorta and force the layers apart. In an aortic dissection, blood penetrates the intima, which is the innermost layer of the aortic artery, and enters the media layer. The high pressure rips the tissue of the media apart along the laminated plane splitting the inner ⅔ and the outer ⅓ of the media apart. This can propagate along the length of the aorta for a variable distance forward or backwards. Dissections that propagate towards the iliac bifurcation (with the flow of blood) are called anterograde dissections and those that propagate towards the aortic root (opposite of the flow of blood) are called retrograde dissections. The initial tear is usually within 100 mm of the aortic valve so a retrograde dissection can easily compromise the pericardium leading to a hemocardium. Aortic dissection is a medical emergency and can quickly lead to death, even with optimal treatment.

Symptoms of aortic dissection are known to those skilled in the art, and include severe pain that had a sudden onset that may be described as tearing in nature, or stabbing or sharp in character. Some individuals will report that the pain migrates as the dissection extends down the aorta. While the pain may be confused with the pain of a myocardial infarction, aortic dissection is usually not associated with the other signs that suggest myocardial infarction, including heart failure, and ECG changes. Individuals experiencing an aortic dissection usually do not present with diaphoresis (profuse sweating). Individuals with chronic dissection may not indicate the presence of pain. Aortic insufficiency is also typically seen. Other less common symptoms that may be seen in the setting of aortic dissection include congestive heart failure (7%), syncope (9%), cerebrovascular accident (3-6%), ischemic peripheral neuropathy, paraplegia, cardiac arrest, and sudden death. Preferably, this diagnosis is made by visualization of the intimal flap on a diagnostic imaging test such as a CT scan of the chest with iodinated contrast material and a trans-esophageal echocardiogram.

An aortic aneurysm, on the other hand, is a cardiovascular disorder characterized by a swelling of the aorta, which is usually caused by an underlying weakness in the wall of the aorta at that location. Aortic aneurysms are classified by where they occur on the aorta. Abdominal aortic aneurysms, hereafter referred to as AAAs, are the most common type of aortic aneurysm, and are generally asymptomatic before rupture. AAAs are attributed primarily to atherosclerosis, though other factors are involved in their formation. An AAA may remain asymptomatic indefinitely. There is a large risk of rupture once the size has reached 5 cm, though some AAAs may swell to over 15 cm in diameter before rupturing. Only 10-25% of patients survive rupture due to large pre- and post-operative mortality.

Symptoms of an aortic aneurysm may include: anxiety or feeling of stress; nausea and vomiting; clammy skin; rapid heart rate. However, an intact aortic aneurysm may not produce symptoms. As they enlarge, symptoms such as abdominal pain and back pain can develop. Compression of nerve roots may cause leg pain or numbness. Untreated, aneurysms tend to become progressively larger, although the rate of enlargement is unpredictable for a given individual. In some cases, clotted blood which lines most aortic aneurysms can break off and result in an embolus. Preferably, medical imaging is used to confirm the diagnosis of an aortic aneurysm.

The present invention also provides a method for characterizing a subject's response to therapy directed at stabilizing or regressing CVD (e.g. such as atherosclerotic CVD), diabetes mellitus, insulin resistance, metabolic syndrome, NAFLD, or NASH. The method comprises determining levels of choline-related trimethylamine-containing compounds (e.g., TMANO, choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine) in a biological sample taken from the subject prior to therapy and determining the level of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in a corresponding biological sample taken from the subject during or following therapy. A decrease in levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the sample taken after or during therapy as compared to levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the sample taken before therapy is indicative of a positive effect of the therapy on cardiovascular disease, diabetes mellitus, insulin resistance, metabolic syndrome, NAFLD, or NASH in the treated subject.

In another embodiment, the present invention relates to kits that include reagents for assessing levels of TMANO, choline, crotonobetaine, gamma-butyrobetaine, carnitine, short chain carnitines (e.g., iC2, C3, and C4), 4-Trimethyl-ammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in biological samples obtained from a test subject. In certain embodiments, the kits also include printed materials such as instructions for practicing the present methods, or information useful for assessing a test subject's risk of CVD, diabetes mellitus, insulin resistance, metabolic syndrome, NAFLD, or NASH. Examples of such information include, but are not limited to cut-off values, sensitivities at particular cut-off values, as well as other printed material for characterizing risk based upon the outcome of the assay. In some embodiments, such kits may also comprise control reagents, e.g. known amounts of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine.

In certain embodiments, levels of choline-related trimethylamine-containing compounds (e.g., TMANO, choline, crotonobetaine, gamma-butyrobetaine, carnitine, short chain carnitines (e.g., iC2, C3, and C4), 4-Trimethylammonium-butyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine) in a biological sample of the test subject are compared to a control value that is derived from levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in comparable biological samples of control subjects. In an alternative embodiment, levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the biological sample of the test subject may then be compared to an internal standard based on levels of other biomolecules in the subject's biological sample. Test subjects whose levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine are above the control value or in the higher range of control values are at greater risk of having or developing cardiovascular disease (e.g. congestive heart failure, aortic aneurysm, etc.), diabetes mellitus, insulin resistance, metabolic syndrome, NAFLD, or NASH than test subjects whose levels of TMANO, choline, crotonobetaine, gamma-butyrobetaine, carnitine, and/or betaine are at or below the control value or in the lower range of control values. Moreover, the extent of the difference between the subject's TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine levels and the control value is also useful for characterizing the extent of the risk and thereby, determining which subjects would most benefit from certain therapies.

In certain embodiments, the subject's risk profile for CVD, diabetes mellitus, pre-diabetes, impaired glucose tolerance, impaired fasting glucose, insulin resistance, metabolic syndrome, NAFLD, or NASH is determined by combining a first risk value, which is obtained by comparing levels of choline-related trimethylamine-containing compounds (e.g., TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine) in a biological sample of the subject with levels of TMANO, choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in a control population, with one or more additional risk values to provide a final risk value. Such additional risk values may be obtained by procedures including, but not limited to, determining the subject's blood pressure, assessing the subject's response to a stress test, determining levels of myeloperoxidase, homocitrulline, nitrotyrosine, C-reactive protein, fibrinogen and PAI-1, homocysteine, asymmetric dimethylarginine, brain natriuretic peptide, low density lipoprotein, or cholesterol in a bodily sample from the subject, or assessing the subject's atherosclerotic plaque burden.

In one embodiment, the method is used to assess the test subject's risk of having cardiovascular disease, and in particular atherosclerotic cardiovascular disease. One form of cardiovascular disease is coronary artery disease. Medical procedures for determining whether a human subject has coronary artery disease or is at risk for experiencing a complication of coronary artery disease include, but are not limited to, coronary angiography, coronary intravascular ultrasound (IVUS), stress testing (with and without imaging), assessment of carotid intimal medial thickening, carotid ultrasound studies with or without implementation of techniques of virtual histology, coronary artery electron beam computer tomography (EBTC), cardiac computerized tomography (CT) scan, CT angiography, cardiac magnetic resonance imaging (MRI), and magnetic resonance angiography (MRA). Because cardiovascular disease is typically not limited to one region of a subject's vasculature, a subject who is diagnosed as having or being at risk of having coronary artery disease is also considered at risk of developing or having other forms of CVD such as cerebrovascular disease, aortic-iliac disease, and peripheral artery disease.

Subjects who are at risk of having cardiovascular disease are at risk of having an abnormal stress test or abnormal cardiac catheterization. Subjects who are at risk of having CVD are also at risk of exhibiting increased carotid intimal medial thickness and coronary calcification, characteristics that can be assessed using non-invasive imaging techniques. Subjects who are at risk of having CVD are also at risk of having an increased atherosclerotic plaque burden, a characteristic that can be examined using intravascular ultrasound.

In another embodiment, the present methods are used to assess a subject's risk of developing cardiovascular disease, diabetes mellitus, insulin resistance, metabolic syndrome, NAFLD, or NASH in the future. In one embodiment, the subject is an apparently healthy individual. In another embodiment, the subject is not otherwise at an elevated risk of having cardiovascular disease, diabetes mellitus, insulin resistance, metabolic syndrome, NAFLD, or NASH.

Embodiments of the present methods can also be used to assess the test subject's risk of experiencing a cardiovascular event within the ensuing three years, two years, or year. In another embodiment, the present methods are used to determine if a subject presenting with chest pain is at risk of experiencing a heart attack or other cardiovascular event, such as a near term myocardial infarction, reinfarction, the need for revascularization, or death. As used in this context, the term "near term" means within one year. Thus, subjects who are at near term risk may be at risk of experiencing a cardiovascular event within the following day, 3 months, or 6 months after presenting with chest pain.

The present invention also provides a method for monitoring over time the status of CVD in a subject who has been diagnosed as having CVD. In this context, the method is also useful for monitoring the risk for atherosclerotic progression or regression in a subject with CVD. In one embodiment, the method comprises determining the levels of TMANO, choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in a biological sample taken from the subject at an initial time and in a corresponding biological sample taken from the subject at a subsequent time. An increase in levels of choline-related trimethylamine-containing compounds (e.g., TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine and/or betaine) in a biological sample taken at the subsequent time as compared to the initial time indicates that the subject's CVD has progressed or worsened. A decrease in levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine indicates that the CVD has improved or regressed. For those subjects who have already experienced a cardiovascular event such as a myocardial infarction or ischemic stroke, such methods can also be used to assess the subject's risk of having a subsequent cardiovascular event. An increase over time in levels of the TMANO, choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the subject indicates that a subject's risk of experiencing a subsequent adverse cardiovascular event has increased. A decrease over time in levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the subject indicates that that the subject's risk of experiencing a subsequent adverse cardiovascular event has decreased.

In another embodiment, the present invention provides a method for evaluating therapy in a subject suspected of having or diagnosed as having cardiovascular disease. The method comprises determining levels one or more choline-related trimethylamine-containing compounds (e.g., TMANO, choline, crotonobetaine, gamma-butyrobetaine, carnitine, short chain carnitines (e.g., iC2, C3, and C4), and/or betaine) in a biological sample taken from the subject prior to therapy and determining levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in a corresponding biological sample taken from the subject during or following therapy. A decrease in levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the sample taken after or during therapy as compared to levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the sample taken before therapy is indicative of a positive effect of the therapy on cardiovascular disease in the treated subject.

Biological Samples

Biological samples include, but are not necessarily limited to bodily fluids such as blood-related samples (e.g., whole blood, serum, plasma, and other blood-derived samples), urine, cerebral spinal fluid, bronchoalveolar lavage, exhaled breath samples, and the like. Another example of a biological sample is a tissue sample. TMANO, choline, crotonobetaine, gamma-butyrobetaine, carnitine, short chain carnitines (e.g., iC2, C3, and C4), 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine and/or betaine levels can be assessed either quantitatively or qualitatively, usually quantitatively. The levels of the choline-related trimethylamine-containing compounds can be determined either in vivo or ex vivo. In certain embodiments, exhaled breath is measured (e.g., by mass spectrometry or related methods). Exhaled breath can be collected in mylar bags, any other type of bag or container, etc., or any type of breath analyzer known in the art.

A biological sample may be fresh or stored (e.g. blood or blood fraction stored in a blood bank). The biological sample may be a bodily fluid expressly obtained for the assays of this invention or a bodily fluid obtained for another purpose which can be sub-sampled for the assays of this invention.

In one embodiment, the biological sample is whole blood. Whole blood may be obtained from the subject using standard clinical procedures. In another embodiment, the biological sample is plasma. Plasma may be obtained from whole blood samples by centrifugation of anti-coagulated blood. Such process provides a buffy coat of white cell components and a supernatant of the plasma. In another embodiment, the biological sample is serum. Serum may be obtained by centrifugation of whole blood samples that have been collected in tubes that are free of anti-coagulant. The blood is permitted to clot prior to centrifugation. The yellowish-reddish fluid that is obtained by centrifugation is the serum. In another embodiment, the sample is urine.

The sample may be pretreated as necessary by dilution in an appropriate buffer solution, heparinized, concentrated if desired, or fractionated by any number of methods including but not limited to ultracentrifugation, fractionation by fast performance liquid chromatography (FPLC), or precipitation of apolipoprotein B containing proteins with dextran sulfate or other methods. Any of a number of standard aqueous buffer solutions at physiological pH, such as phosphate, Tris, or the like, can be used.

Subjects

The subject is any human or other animal to be tested for characterizing its risk of CVD (e.g. congestive heart failure, aortic aneurysm or aortic dissection), diabetes mellitus, insulin resistance, metabolic syndrome, NAFLD, or NASH. In certain embodiments, the subject does not otherwise have an elevated risk of an adverse cardiovascular event. Subjects having an elevated risk of experiencing a cardiovascular event include those with a family history of cardiovascular disease, elevated lipids, smokers, prior acute cardiovascular event, etc. (See, e.g., Harrison's Principles of Experimental Medicine, 15th Edition, McGraw-Hill, Inc., N.Y.—hereinafter "Harrison's").

In certain embodiments the subject is apparently healthy. "Apparently healthy", as used herein, describes a subject who does not have any signs or symptoms of CVD, diabetes mellitus, insulin resistance, metabolic syndrome, NAFLD, or NASH, or has not previously been diagnosed as having any signs or symptoms indicating the presence of atherosclerosis, such as angina pectoris, history of a cardiovascular event such as a myocardial infarction or stroke, or evidence of atherosclerosis by diagnostic imaging methods including, but not limited to coronary angiography. Apparently healthy subjects also do not have any signs or symptoms of having heart failure or an aortic disorder.

In other embodiments, the subject already exhibits symptoms of cardiovascular disease. For example, the subject may exhibit symptoms of heart failure or an aortic disorder such as aortic dissection or aortic aneurysm. For subjects already experiencing cardiovascular disease, the levels of choline-related trimethylamine-containing compounds can be used to predict the likelihood of further cardiovascular events or the outcome of ongoing cardiovascular disease.

In certain embodiments, the subject is a nonsmoker. "Nonsmoker" describes an individual who, at the time of the evaluation, is not a smoker. This includes individuals who have never smoked as well as individuals who have smoked but have not used tobacco products within the past year. In certain embodiments, the subject is a smoker.

In some embodiments, the subject is a nonhyperlipidemic subject. "Nonhyperlipidemic" describes a subject that is a nonhypercholesterolemic and/or a nonhypertriglyceridemic subject. A "nonhypercholesterolemic" subject is one that does not fit the current criteria established for a hypercholesterolemic subject. A nonhypertriglyceridemic subject is one that does not fit the current criteria established for a hypertriglyceridemic subject (See, e.g., Harrison's Principles of Experimental Medicine, 15th Edition, McGraw-Hill, Inc., N.Y.—hereinafter "Harrison's"). Hypercholesterolemic subjects and hypertriglyceridemic subjects are associated with increased incidence of premature coronary heart disease. A hypercholesterolemic subject has an LDL level of >160 mg/dL, or >130 mg/dL and at least two risk factors selected from the group consisting of male gender, family history of premature coronary heart disease, cigarette smoking (more than 10 per day), hypertension, low HDL (<35 mg/dL), diabetes mellitus, hyperinsulinemia, abdominal obesity, high lipoprotein (a), and personal history of cerebrovascular disease or occlusive peripheral vascular disease. A hypertriglyceridemic subject has a triglyceride (TG) level of >250 mg/dL. Thus, a nonhyperlipidemic subject is defined as one whose cholesterol and triglyceride levels are below the limits set as described above for both the hypercholesterolemic and hypertriglyceridemic subjects.

Methods for Measuring Levels of Choline-Related Trimethylamine-Containing Compounds The levels of choline-related trimethylamine-containing compounds can be measured using any suitable analytic method, including standard methods known in the art. For example, the levels of TMANO, choline, crotonobetaine (trans and cis), gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and betaine in a subject can be measured using an analytic device, which is a machine including a detector capable of identifying small organic molecules such as choline-related trimethylamine-containing compounds. The analytic device may be a spectrometric device, such as a mass spectrometer, an ultraviolet spectrometer, or a nuclear magnetic resonance spectrometer. A spectrometer is a device that uses a spectroscopic technique to assess the concentration or amount of a given species in a medium such as a biological sample (e.g., a bodily fluid). The analytic device used to measure the levels of choline-related trimethylamine-containing compounds can be either a portable or a stationary device. In addition to including equipment used for detecting the choline-related trimethylamine-containing compounds, the analytic device can also include additional equipment to provide physical separation of analytes prior to analysis. For example, if the analyte detector is a mass spectrometer, it may also include a high performance liquid chromatograph (HPLC) or gas chromatograph (GC) to purify the choline-related trimethylamine-containing compounds before their detection by mass spectrometry.

As indicated herein, mass spectrometry-based methods can be used to assess levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in a biological sample. Mass spectrometers include an ionizing source (e.g., electrospray ionization), an analyzer to separate the ions formed in the ionization source according to their mass-to-charge (m/z) ratios, and a detector for the charged ions. In tandem mass spectrometry, two or more analyzers are included. Such methods are standard in the art and include, for example, HPLC with on-line electrospray ionization (ESI) and tandem mass spectrometry.

Other spectrometric methods can also be used to detect choline-related trimethylamine-containing compounds. For example, choline-related trimethylamine-containing compounds can be measured by HPLC using a variety of detectors including, but not limited to UV or V is (of a derivatized form), mass spectrometry, or GC/MS. Another method that can be used to identify choline-related trimethylamine-containing compounds is nuclear magnetic resonance (NMR). Examples of NMR include proton NMR and carbon-13 NMR.

Once the levels of choline-related trimethylamine-containing compounds have been determined, they can be displayed in a variety of ways. For example, the levels of choline-related trimethylamine-containing compounds can be displayed graphically on a display as numeric values or proportional bars (i.e., a bar graph) or any other display method known to those skilled in the art. The graphic display can provide a visual representation of the amount of the choline-related trimethylamine-containing compound (e.g., TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, or betaine) in the biological sample being evaluated. In addition, in some embodiments, the analytic device can also be configured to display a comparison of the levels of TMANO in the subject's bodily fluid to a control value based on levels of TMANO in comparable bodily fluids from a reference cohort.

Control Value

In certain embodiments, levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in the biological sample obtained from the test subject may compared to a control value. A control value is a concentration of an analyte that represents a known or representative amount of an analyte. For example, the control value can be based upon levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in comparable samples obtained from a reference cohort. In certain embodiments, the reference cohort is the general population. In certain embodiments, the reference cohort is a select population of human subjects. In certain embodiments, the reference cohort is comprised of individuals who have not previously had any signs or symptoms indicating the presence of atherosclerosis, such as angina pectoris, history of a cardiovascular event such as a myocardial infarction or stroke, evidence of atherosclerosis by diagnostic imaging methods including, but not limited to coronary angiography. In certain embodiments, the reference cohort includes individuals, who if examined by a medical professional would be characterized as free of symptoms of disease (e.g., cardiovascular disease). In another example, the reference cohort may be individuals who are nonsmokers (i.e., individuals who do not smoke cigarettes or related items such as cigars). A nonsmoker cohort may have a different normal range of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine than will a smoking population or the general population. Accordingly, the control values selected may take into account the category into which the test subject falls. Appropriate categories can be selected with no more than routine experimentation by those of ordinary skill in the art.

The control value is preferably measured using the same units used to characterize the level of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine and/or betaine obtained from the test subject. Thus, if the level of the TMANO is an absolute value such as the units of TMANO, choline, and/or betaine per ml of blood, the control value is also based upon the units of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine per ml of blood in individuals in the general population or a select population of human subjects.

The control value can take a variety of forms. The control value can be a single cut-off value, such as a median or mean. The control value can be established based upon comparative groups such as where the risk in one defined group is double the risk in another defined group. The control values can be divided equally (or unequally) into groups, such as a low risk group, a medium risk group and a high-risk group, or into quadrants, the lowest quadrant being individuals with the lowest risk the highest quadrant being individuals with the highest risk, and the test subject's risk of having CVD can be based upon which group his or her test value falls. Control values of TMANO in biological samples obtained, such as mean levels, median levels, or "cut-off" levels, are established by assaying a large sample of individuals in the general population or the select population and using a statistical model such as the predictive value method for selecting a positively criterion or receiver operator characteristic curve that defines optimum specificity (highest true negative rate) and sensitivity (highest true positive rate) as described in Knapp, R. G., and Miller, M. C. (1992). Clinical Epidemiology and Biostatistics. William and Wilkins, Harual Publishing Co. Malvern, Pa., which is specifically incorporated herein by reference. A "cutoff" value can be determined for each risk predictor that is assayed.

Comparison of a Choline-Related Trimethylamine-Containing Compound Obtained from a Subject to a Control Value Levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in a subject's biological sample may be compared to a single control value or to a range of control values. If the level of the present risk predictor in the test subject's biological sample is greater than the control value or exceeds or is in the upper range of control values, the test subject is at greater risk of developing or having CVD (or diabetes mellitus, insulin resistance, metabolic syndrome, NAFLD, or NASH) or experiencing a cardiovascular event within the ensuing year, two years, and/or three years than individuals with levels comparable to or below the control value or in the lower range of control values. In contrast, if levels of the present risk predictor in the test subject's biological sample is below the control value or is in the lower range of control values, the test subject is at a lower risk of developing or having CVD (or diabetes mellitus, insulin resistance, metabolic syndrome, NAFLD, or NASH) or experiencing a cardiovascular event within the ensuing year, two years, and/or three years than individuals whose levels are comparable to or above the control value or exceeding or in the upper range of control values. The extent of the difference between the test subject's risk predictor levels and control value is also useful for characterizing the extent of the risk and thereby determining which individuals would most greatly benefit from certain aggressive therapies. In those cases, where the control value ranges are divided into a plurality of groups, such as the control value ranges for individuals at high risk, average risk, and low risk, the comparison involves determining into which group the test subject's level of the relevant risk predictor falls.

Another type of control value is an internal standard in the sample. An internal standard is a known amount of another compound that can be provided in a sample that can be measured along with the analyte to serve as a reference. The diagnostic methods described herein can also be carried out by determining the levels of TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine in a subject's biological sample and comparing them to the amount of an internal standard.

Evaluation of Therapeutic Agents

Also provided are methods for evaluating the effect of CVD, diabetes mellitus, insulin resistance, metabolic syndrome, NAFLD, or NASH therapeutic agents on individuals who have been diagnosed as having or as being at risk of developing CVD, diabetes mellitus, insulin resistance, metabolic syndrome, NAFLD, or NASH. Such therapeutic agents include, but are not limited to, antibiotics, anti-inflammatory agents, insulin sensitizing agents, antihypertensive agents, anti-thrombotic agents, anti-platelet agents, fibrinolytic agents, lipid reducing agents, direct thrombin inhibitors, ACAT inhibitor, CDTP inhibitor thioglytizone, glycoprotein IIb/IIIa receptor inhibitors, agents directed at raising or altering HDL metabolism such as apoA-I milano or CETP inhibitors (e.g., torcetrapib), or agents designed to act as artificial HDL. Accordingly, a CVD therapeutic agent, as used herein, refers to a broader range of agents that can treat a range of cardiovascular-related conditions, and may encompass more compounds than the traditionally defined class of cardiovascular agents.

Evaluation of the efficacy of CVD, diabetes mellitus, insulin resistance, metabolic syndrome, NAFLD, or NASH therapeutic agents can include obtaining a predetermined value of the choline-related trimethylamine-containing compound or compounds in a biological sample, and determining the level of one or more choline-related trimethylamine-containing compounds in a corresponding biological fluid taken from the subject following administration of the therapeutic agent. A decrease in the level of one or more of the choline-related trimethylamine-containing compounds in the sample taken after administration of the therapeutic as compared to the level of the selected risk markers in the sample taken before administration of the therapeutic agent is indicative of a positive effect of the therapeutic agent on cardiovascular disease, diabetes mellitus, insulin resistance, metabolic syndrome, NAFLD, or NASH in the treated subject.

A predetermined value can be based on the levels of one or more choline-related trimethylamine-containing compounds in a biological sample taken from a subject prior to administration of a therapeutic agent. In another embodiment, the predetermined value is based on the levels of one or more choline-related trimethylamine-containing compounds in comparable biological samples taken from control subjects that are apparently healthy, as defined herein.

Embodiments of the methods described herein can also be useful for determining if and when therapeutic agents that are targeted at preventing CVD (or diabetes mellitus, insulin resistance, metabolic syndrome, NAFLD, or NASH) or for slowing the progression of CVD should and should not be prescribed for a individual. For example, individuals with TMANO, choline, crotonobetaine, gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine values above a certain cutoff value, or that are in the higher tertile or quartile of a "normal range," could be identified as those in need of more aggressive intervention with lipid lowering agents, insulin, life style changes, etc.

Drug Screening and Therapeutics

In some embodiments, the present invention provides drug screening assays (e.g., to screen for TMA formation inhibitor drugs). The screening methods of the present invention utilize trimethylamine containing precursors (e.g., TMANO, choline, crotonobetaine (cis and trans), gamma-butyrobetaine, carnitine, 4-Trimethylammoniumbutyraldehyde, dehydrocarnitine, 3-hydroxy-N6-Trimethyl-lysine, N6-Trimethyl-lysine, trimethylammoniumacetone, decarboxycarnitine, phosphocholine, betaine Aldehyde, glycerophosphocholine, phosphatidylcholine, and/or betaine) incubated with intestinal microflora capable of cleaving choline-related TMA-containing compounds to form trimethylamine. For example, in some embodiments, the present invention provides methods of screening for compounds that inhibit the ability of the microflora from cleaving TMA containing precursors to form TMA. In some embodiments, candidate compounds are antibiotic compounds. In other embodiments, candidate compounds are small molecules (e.g., from a small molecule library).

In one screening method, candidate compounds are evaluated for their ability to inhibit TMA formation by microflora by contacting a candidate compound with a sample containing the microflora and TMA containing precursors and then assaying for the effect of the candidate compounds on TMA formation. In some embodiments, the effect of candidate compounds on TMA formation is assayed for by detecting the level of TMA formed.

Specifically, the present invention provides screening methods for identifying modulators, i.e., candidate or test compounds or agents (e.g., proteins, peptides, peptidomimetics, peptoids, small molecules, antibiotics, or other drugs) which prevent intestinal microflora from forming TMA from precursor TMA containing molecules. Compounds which inhibit the formation of TMA by intestinal microflora are useful in the treatment of cardiovascular diseases, diabetes mellitus, insulin resistance, metabolic syndrome, NAFLD, or NASH.

The test compounds of the present invention can be obtained using any of the numerous approaches in combinatorial library methods known in the art, including biological libraries; peptoid libraries (libraries of molecules having the functionalities of peptides, but with a novel, non-peptide backbone, which are resistant to enzymatic degradation but which nevertheless remain bioactive; see, e.g., Zuckennann et al., J. Med. Chem. 37: 2678-85 (1994)); spatially addressable parallel solid phase or solution phase libraries; synthetic library methods requiring deconvolution; the 'one-bead one-compound' library method; and synthetic library methods using affinity chromatography selection. The biological library and peptoid library approaches are preferred for use with peptide libraries, while the other four approaches are applicable to peptide, non-peptide oligomer or small molecule libraries of compounds (Lam (1997) Anticancer Drug Des. 12:145).

In certain embodiments, the test compounds are antibiotics. Any type of antibiotic may be screened. Examples of such antibiotics include, but are not limited to, Ampicillin; Bacampicillin; Carbenicillin Indanyl; Mezlocillin; Piperacillin; Ticarcillin; Amoxicillin-Clavulanic Acid; Ampicillin-Sulbactam; Benzylpenicillin; Cloxacillin; Dicloxacillin; Methicillin; Oxacillin; Penicillin G; Penicillin V; Piperacillin Tazobactam; Ticarcillin Clavulanic Acid; Nafcillin; Cephalosporin I Generation; Cefadroxil; Cefazolin; Cephalexin; Cephalothin; Cephapirin; Cephradine; Cefaclor; Cefamandol; Cefonicid; Cefotetan; Cefoxitin; Cefprozil; Ceftmetazole; Cefuroxime; Loracarbef; Cefdinir; Ceftibuten; Cefoperazone; Cefixime; Cefotaxime; Cefpodoxime proxetil; Ceftazidime; Ceftizoxime; Ceftriaxone; Cefepime; Azithromycin; Clarithromycin; Clindamycin; Dirithromycin; Erythromycin; Lincomycin; Troleandomycin; Cinoxacin; Ciprofloxacin; Enoxacin; Gatifloxacin; Grepafloxacin; Levofloxacin; Lomefloxacin; Moxifloxacin; Nalidixic acid; Norfloxacin; Ofloxacin; Sparfloxacin; Trovafloxacin; Oxolinic acid; Gemifloxacin; Perfloxacin; Imipenem-Cilastatin Meropenem; Aztreonam; Amikacin; Gentamicin; Kanamycin; Neomycin; Netilmicin; Streptomycin; Tobramycin; Paromomycin; Teicoplanin; Vancomycin; Demeclocycline; Doxycycline; Methacycline; Minocycline; Oxytetracycline; Tetracycline; Chlortetracycline; Mafenide; Silver Sulfadiazine; Sulfacetamide; Sulfadiazine; Sulfamethoxazole; Sulfasalazine; Sulfisoxazole; Trimethoprim-Sulfamethoxazole; Sulfamethizole; Rifabutin; Rifampin; Rifapentine; Linezolid; Streptogramins; Quinopristin Dalfopristin; Bacitracin; Chloramphenicol; Fosfomycin; Isoniazid; Methenamine; Metronidazol; Mupirocin; Nitrofurantoin; Nitrofurazone; Novobiocin; Polymyxin; Spectinomycin; Trimethoprim; Colistin; Cycloserine; Capreomycin; Ethionamide; Pyrazinamide; Para-aminosalicyclic acid; and Erythromycin ethylsuccinate.

Examples of methods for the synthesis of molecular libraries can be found in the art, for example in: DeWitt et al., Proc. Natl. Acad. Sci. U.S.A. 90:6909 (1993); Erb et al., Proc. Nad. Acad. Sci. USA 91:11422 (1994); Zuckermann et al., J. Med. Chem. 37:2678 (1994); Cho et al., Science 261:1303 (1993); Carrell et al., Angew. Chem. Int. Ed. Engl. 33.2059 (1994); Carell et al., Angew. Chem. Int. Ed. Engl. 33:2061 (1994); and Gallop et al., J. Med. Chem. 37:1233 (1994).

Libraries of compounds may be presented in solution (e.g., Houghten, Biotechniques 13:412-421 (1992)), or on beads (Lam, Nature 354:82-84 (1991)), chips (Fodor, Nature 364:555-556 (1993)), bacteria or spores (U.S. Pat. No. 5,223,409; herein incorporated by reference), plasmids (Cull et al., Proc. Nad. Acad. Sci. USA 89:18651869 (1992)) or on phage (Scott and Smith, Science 249:386-390 (1990); Devlin Science 249:404-406 (1990); Cwirla et al., Proc. Natl. Acad. Sci. 87:6378-6382 (1990); Felici, J. Mol. Biol. 222: 301 (1991)).

The ability of the test compound to inhibit TMA formation by intestinal microflora can be monitored by detectably labeling the TMA portion of a TMA containing precursor compound. Such detectable labels include, for example, radioisotopes, chromophores, fluorophores, or enzymatic labels. For example, TMA containing precursors can be labeled with $^{125}I$, $^{35}S$ $^{14}C$ or $^{3}H$, either directly or indirectly, and the radioisotope detected by direct counting of radioemmission or by scintillation counting. Alternatively, TMA containing precursor can be enzymatically labeled with, for example, horseradish peroxidase, alkaline phosphatase, or luciferase, and the enzymatic label detected by determination of conversion of an appropriate substrate to product.

In one embodiment, the TMA containing precursor or the test substance is anchored onto a solid phase. The TMA containing precursor anchored on the solid phase can be detected at the end of the reaction.

In certain embodiments, cell free assays can be conducted in a liquid phase. In such an assay, the reaction products are separated from unreacted components, by any of a number of standard techniques, including, but not limited to: differential centrifugation (see, for example, Rivas and Minton, Trends Biochem Sci 18:284-7 (1993)); chromatography (gel filtration chromatography, ion-exchange chromatography); electrophoresis (see, e.g., Ausubel et al., eds. Current Protocols in Molecular Biology 1999, J. Wiley: New York.); and immunoprecipitation (see, for example, Ausubel et al., eds. Current Protocols in Molecular Biology 1999, J. Wiley: New York). Such resins and chromatographic techniques are known to one skilled in the art (See e.g., Heegaard J. Mol. Recognit. 11:141-8 (1998); Hageand Tweed J. Chromatogr. Biomed. Sci. Appl 699:499-525 (1997)).

This invention further pertains to agents identified by the above-described screening assays. Accordingly, it is within the scope of this invention to further use an agent identified as described herein in an appropriate animal model to determine the efficacy, toxicity, side effects, or mechanism of action, of treatment with such an agent. Furthermore, novel agents identified by the above-described screening assays can be used for treatments as described herein.

EXAMPLES

The following examples are for purposes of illustration only and are not intended to limit the scope of the claims.

Example 1

Based on the following studies, it was determined that levels of a compound called TMANO (trimethylamine-N-oxide) in a biological sample (e.g., plasma, serum, whole blood, or urine), can serve as a predictor of cardiovascular disease risk both for short term adverse outcomes, such as the evaluation of a patient presenting with chest pain, for near term evaluation, and for longer term outcomes for lower risk populations, such as those obtained in community based screenings, or in subjects undergoing elective diagnostic cardiovascular procedures like angiography, cardiac CT, stress testing, or myocardial perfusion studies.

TMANO levels predict the risk of having CVD, such as Coronary Artery Disease (CAD) and/or Peripheral Artery Disease (PAD), as well as the risk of developing an adverse event from CVD including non-fatal myocardial infarction (MI), stroke, the need for revascularization, or death.

TMANO levels can also be used to monitor CVD therapies and the response to anti-inflammatory and other cardiovascular risk-reducing interventions.

TMANO was discovered through a series of metabolomics studies. An effort was made to define low molecular weight analytes in plasma, serum, blood or urine whose levels would predict cardiovascular disease (CVD). A "learning set" of 50% cases to 50% controls was used, where cases were defined by subjects who experience a cardiovascular event in the ensuing 3 year period, such as experiencing a non-fatal MI, stroke, revascularization event (CABG, angioplasty, stent) or death, and controls who were individuals lacking such events. Initial subjects examined were from a large clinical repository of sequential subjects undergoing elective diagnostic cardiac catheterization and for whom outcome data was available.

Initially, proteins were removed from plasma and the low molecular weight components (<1000) analyzed by Liquid Chromatography-Mass Spectrometry (LC/MS) analysis. Each analyte having a molecular weight eluting under 1000 was noted for retention time and m/z, and signal of ionization. The results obtained for the cases were then compared to those obtained for the controls.

Shown in FIG. 1 is a plot of only the analytes monitored between m/z 50 and 100. The top panel (a) indicates magnitude of the signal. There was interest in identifying analytes in the plasma that could distinguish between cases and controls, and for which a large signal was seen. The middle panel (b) shows the -logP value of levels in the 4th vs 1st quartile for each analyte in this m/z range. These were evaluated to identify an analyte that was predictive of CVD risks, and thus had a significant P value (i.e., -logP> than 1.3, which corresponds to P<0.05). The bottom panel (c) indicates the odds ratio (95% confidence interval) for analytes in this m/z range for 4th quartile vs. 1st quartile levels of each analyte. The analytes providing higher Odds Ratios (ORs) and confidence intervals (CIs) are significant. FIG. 1 shows several analytes that might be suitable to select between cases and controls. The identification of the analyte exhibiting m/z 76 was pursued because it showed a high signal, significant separation of cases from controls, and a large odds ratio for the prediction of a cardiovascular event.

The data provided in FIG. 1 was obtained by reverse phase HPLC coupled to API 365 triple quadrupole mass spectrometer (Applied Biosystems, Foster, Calif.) with Ionics EP 10+ upgrade (Concord) in positive ESI-MS ion mode. Plasma supernatant (20 μl) after precipitation with 80% methanol was injected onto a Phenyl column (4.6×250 mm, 5 pm Rexchrom Phenyl) (Regis) at a flow rate of 0.8 ml/min. The separation was performed using a gradient starting from 10 mM ammonium formate over 0.5 min, then to 5 mM ammonium formate, 25% methanol and 0.1% formic acid over 3 min, held for 8 min, followed by 100% methanol and water washing for 3 min each. The eluate in the initial 4 min from HPLC column was switched off, and only the eluate from 4 to 11 min was applied to data acquisition by mass spectrometer. With regard to panel (b), significant levels for the difference in each extracted ion between 50 controls who underwent diagnostic cardiac catheterization and failed to experience a major adverse cardiac event over the ensuing 3 years following study enrollment and 50 cases who experienced a major adverse cardiac event (MACE, the composite of non-fatal MI, stroke, need for revascularization or death) in the 3 year period following study enrollment. With regard to panel (c), dds ratio of prospect risk for MACE, revascularization (Revasc), non-fatal MI or stroke, death, according to the extracted ion peak area. Odds ratio (ORs) and confidential intervals (CIs) were calculated using logistic regression models comparing the risk of the highest quartiles to the lowest quartile.

Figure 2A:
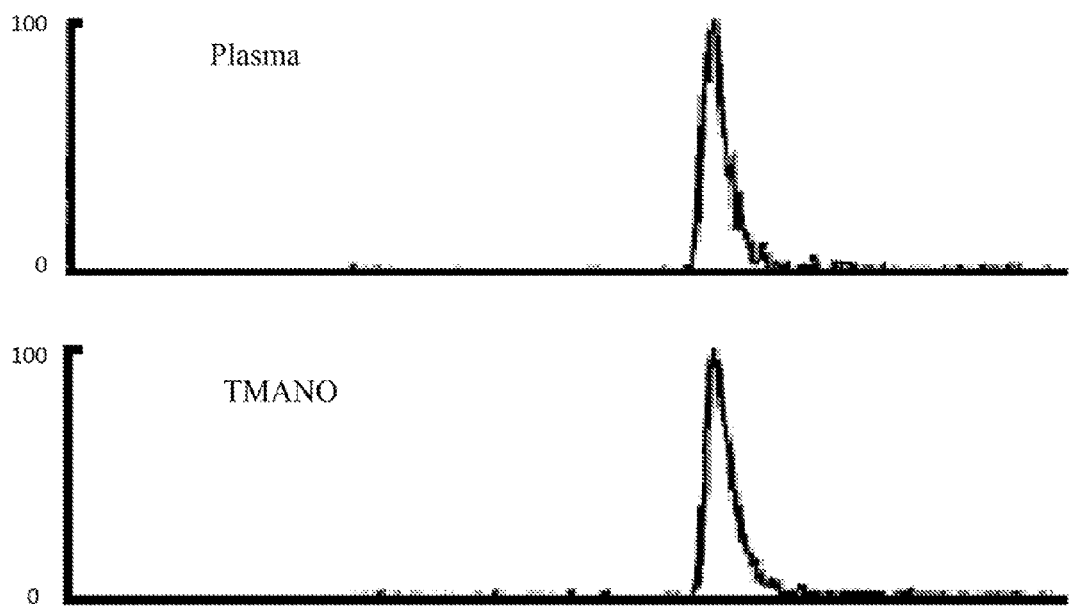
FIG. 2(a-c) provides graphs showing the results of extracted ion chromatograms in positive-ion MS1 mode at m/z=76. The component with m/z=76 was identified by reverse phase HPLC coupled to a mass spectrometer.
Figure 2:
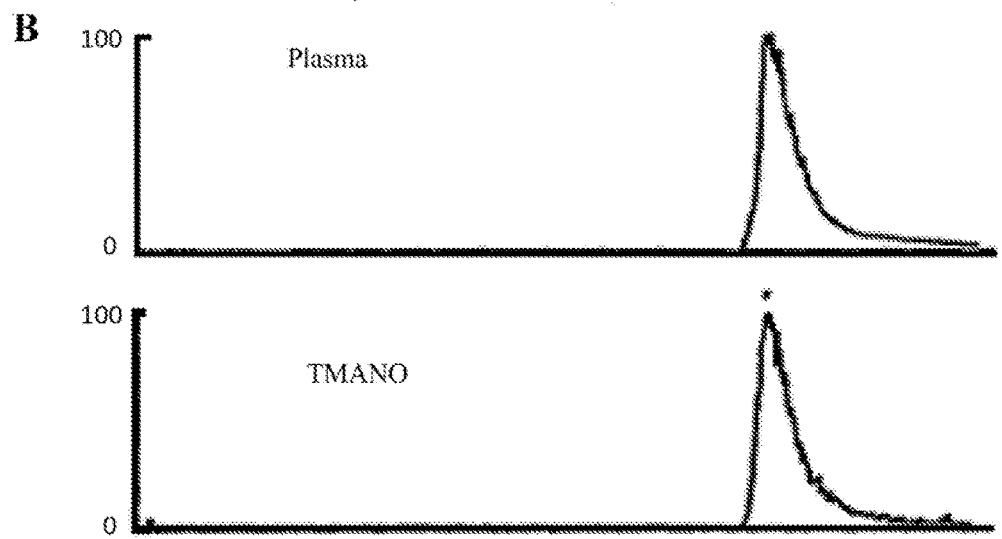
Figure 2:
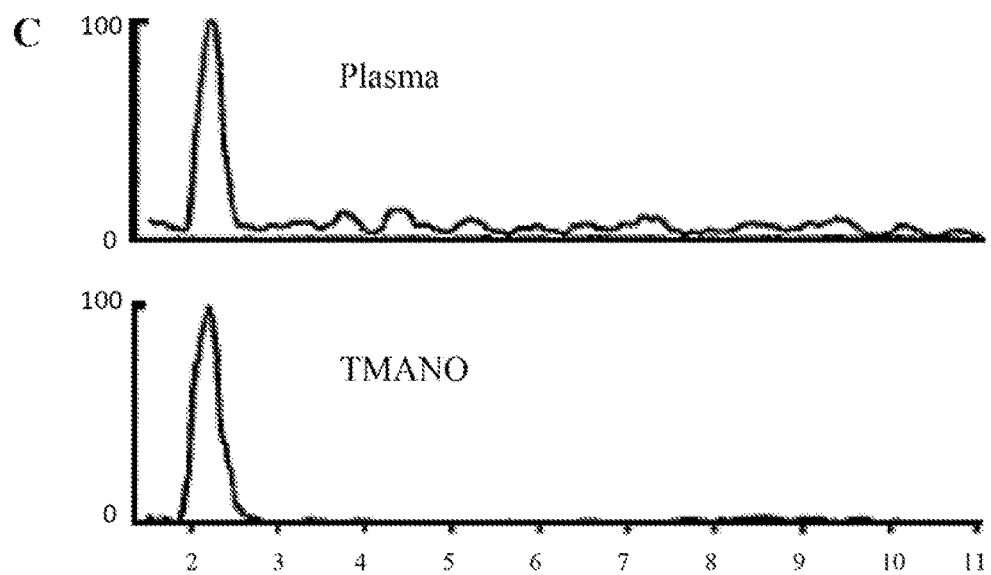

Shown in FIG. 2 are chromatographs indicating the analyte with m/z 76 in plasma that tracks with cardiac risk has similar chromatographic characteristics to TMANO in 3 separate column/mobile phase combinations, and that the analyte appears to be a single species, as evidenced by having a single peak.

The data provided in FIG. 2 was obtained by reverse phase HPLC coupled to API 365 triple quadrupole mass spectrometer (Applied Biosystems, Foster, Calif.) with Ionics EP 10+ upgrade (Concord) in positive ESI-MS ion mode. Plasma supernatant (20 μl) after precipitation with 80% methanol or 20 μl trimethylamine N-oxide (TMANO) stand was injected onto a Phenyl column (4.6×250 mm, 5 pm Rexchrom Phenyl) (Regis) at a flow rate of 0.8 ml/min(a-b) or Prodigy 5 u ODS (2) column (150×2.00 mm, 5 micron) at a flow rate of 0.2 ml/min (c). The separation in panel a was performed using a gradient starting from 10 mM ammonium formate over 0.5 min, then to 5 mM ammonium formate, 25% methanol and 0.1% formic acid over 3 min, held for 8 min, followed by 100% methanol and water washing for 3 mm each. The separation in panel b was performed using a gradient starting from 0.1% formic acid over 2 min, then to 18% acetonitrile with 0.1% formic acid over 18 min, followed by 100% acetonitrile and water washing for 3 min each. starting from 0.1% formic acid over 2 min, then to 18% acetonitrile with 0.1% formic acid over 18 min, followed by 100% acetonitrile and water washing for 6 min each. The separation in panel c was performed using a gradient starting from 0.1% formic acid to 50% acetonitrile with 0.1% formic acid over 18 min, followed by 100% acetonitrile and water washing for 3 min each. starting from 0.1% formic acid over 2 min, then to 18% acetonitrile with 0.1% formic acid over 18 mm, followed by 100% acetonitrile and water washing for 3 min each.

Table 1a provides conformation that the component isolated from plasma that tracks with incident CVD risks is TMANO and not another isomer with identical molecular weight and elemental composition. Note that only TMANO shows identical parent and daughter ions with retention time in 3 different solvent systems comparable to the analyte isolated from plasma that predicts CVD risks.

TABLE 1a

LC-MS characteristics of the positive protonated parental ion at m/z = 76

| Component | Structure | MH+ | System 1 RT (min) | System 1 Product-ions | System 2 RT (min) | System 2 Product ions | System 3 RT (min) | System 3 Product ions |
|---|---|---|---|---|---|---|---|---|
| Component Purified from Plasma | | 76.1097 | 7.6 | 58, 59 | 8.4 | 58, 59 | 1.8 | 58, 59 |
| TMANO | $(CH_3)_3N \rightarrow O$ | 76.1097 | 7.6 | 58, 59 | 8.4 | 58, 59 | 1.8 | 58, 59 |
| 1-Amino-2-propanol | $H_2NCH_2CH(OH)CH_3$ | 76.1097 | 6.0 | 58, 59 | 6.2 | 58, 59 | 1.8 | 58, 59 |
| 2-Amino-1-propanol | $CH_3CH(NH_2)CH_2OH$ | 76.1097 | 6.0 | 58, 59 | 6.2 | 58, 59 | 1.8 | 58, 59 |
| 3-Amino-1-propanol | $H_2NCH_2CH_2CH_2OH$ | 76.1097 | 6.0 | 58, 59 | 6.2 | 58, 59 | 1.8 | 58, 59 |
| Methyl-aminoethanol | $CH_3NHCH_2CH_2OH$ | 76.1097 | 6.5 | 58 | 6.7 | 58 | 1.8 | 58 |
| Glycolamide | $HOCH_2CONH_2$ | 76.1097 | 4.2 | 58 | 4.1 | 58 | 2.2 | 58 |
| Hydroxy-guanidine | $HONHC(=NH)NH_2$ | 76.1097 | 5.7 | 58, 59 | 5.8 | 58, 59 | 1.8 | 58, 59 |
| Glycine | $H_2NCH_2COOH$ | 76.1097 | 3.2 | 58, 59 | 2.0 | 59 | 2.5 | 59 |
| N-Isopropyl-hydroxylamine | $(CH_3)_2CHNOH$ | 76.1097 | 3.0 | 58 | 2.1 | 58, 59 | 1.9 | 59 |

System 1: Regis RexChrom Phenyl HPLC column (25 cm×4.6 mm, 5 micron, 100 A). The separation was performed using gradient 0-0.5 min: 10 mM Ammonium formate; 0.5-3.5 min: linearly changed to 25% methanol with 5 mM ammonium formate and 0.1% formic acid and held for 8 min; 11.5-14 min: linearly changed to 100% methanol with 10 mM ammonium formate and held for 3 min; 17-20 min, 10 mM ammonium formate in water. The flow rate is 0.8 ml/min.

System 2: Regis RexChrom Phenyl HPLC column (25 cm×4.6 mm, 5 micron, 100 A). The separation was performed using gradient starting from 0.1% formic acid over 2 min, then to 18% acetonitrile with 0.1% formic acid over 18 min, followed by 100% acetonitrile and water washing for 3 min each. starting from 0.1% formic acid over 2 min, then to 18% acetonitrile with 0.1% formic acid over 18 min, followed by 100% acetonitrile and water washing for 6 min each. The flow rate is 0.8 ml/min.

System 3: Prodigy 5 u ODS (2) column (150×2.00 mm, 5 micron). The separation was performed using gradient starting from 0.1% formic acid to 50% acetonitrile with 0.1% formic acid over 18 min, followed by 100% acetonitrile and water washing for 3 min each, starting from 0.1% formic acid over 2 min, then to 18% acetonitrile with 0.1% formic acid over 18 min, followed by 100% acetonitrile and water washing for 3 min each. The flow rate is 0.2 ml/min.

Table 1b provides further independent confirmation that the component isolated from plasma that tracks with incident CVD risks is TMANO and not another isomer with identical molecular weight and elemental composition. Note that only TMANO shows identical parent and daughter ions with retention time as the analyte isolated from plasma that predicts CVD risks. The isolated plasma component and the structures depicted of isomers with identical molecular weight and elemental composition were analyzed by GC MS following two distinct derivatization strategies. The results of Tables 1a and 1b unambiguously identify the isolated plasma component that predicts incident CVD risk as TMANO.

TABLE 1b

GC-MS analysis of the peak from plasma that predicts incident CVD risks, and compounds with the same molecular weight of 75 (M+ = 76).

| Component | Structure | System 1 Derivative | System 1 RT (min) | System 2 Derivative | System 2 RT (min) |
|---|---|---|---|---|---|
| Component Purified from Plasma | | ND | | N,N-dimthyl trichloroethylcarbmate | 4.3 |
| TMANO | $(CH_3)_3N? O$ | ND | | N,N-dimthyl trichloroethylcarbmate | 4.3 |
| 1-Amino-2-propanol | $H_2NCH_2CH(OH)CH_3$ | TMS- | 4.4 | ND | |
| 2-Amino-I-propanol | $CH_3CH(NH_2)CH_2OH$ | DiTMS- | 3.8 | ND | |
| 3-Amino-I-propanol | $H_2NCH_2CH_2CH_2OH$ | DiTMS- | 3.7 | ND | |
| Methyl-aminoethanol | $CH_3NHCH_2CH_2OH$ | TMS- | 5.2 | ND | |
| Glycolamide | $HOCH_2CONH_2$ | DiTMS- | 5.3 | ND | |
| Hydroxy-guanidine | $HONHC(=NH)NH_2$ | TMS- | 4.3 | ND | |

TABLE 1b-continued

GC-MS analysis of the peak from plasma that predicts incident CVD risks, and compounds with the same molecular weight of 75 (M+ = 76).

| | | System 1 | | System 2 | |
|---|---|---|---|---|---|
| Component | Structure | Derivative | RT (min) | Derivative | RT (min) |
| Glycine | $H_2NCH_2COOH$ | TriTMS- | 5.3 | ND | |
| N-Isopropyl-hydroxylamine | $(CH_3)_2CHNOH$ | TMS- | 4.3 | ND | |

All compounds were derivatized by trimethylchlorosilane (TMCS, system 1) or tricholoroethyl chloroformate (TCECF, system 2)

System 1, the components reacted with Sylon HTP kit (Supelco, LB44596) containing HMDS, TMCS, Pyridine at 90° C. for 9 hours. GC-MS analysis of the TMS derivatives was performed on a Hewlett Packard (Palo Alto, Calif.) 5973 mass spectrometer coupled to a Hewlett Packard 6890 gas chromatograph using the positive ion chemical ionization mode with methane as the reagent gas. The source temperature was set at 250° C. The TMS derivatives were separated on a J&W Scientific (Folsom, Calif.) DB-1 column (20.0 m, 0.18 mm inner diameter, 0.18-pm film thickness). The injector and the transfer line temperatures were maintained at 320° C. The GC oven was maintained at 60° C. for 2 min, increased at a rate of 20° C./min to 300° C.

System 2, the components was reacted with titanium (III) chloride and then with tricholoroethyl chloroformate (TCECF). The product was dissolved in toluene. GC-MS analysis of the TMS derivatives was performed on a Hewlett Packard (Palo Alto, Calif.) 5973 mass spectrometer coupled to a Hewlett Packard 6890 gas chromatograph using the positive ion chemical ionization mode with methane as the reagent gas. The source temperature was set at 250° C. The TMS derivatives were separated on an Agilent HP-1 Methyl Siloxane column (12.0 m, 0.20 mm inner diameter, 0.33-ttm film thickness). The injector and the transfer line temperatures were maintained at 250° C. The GC oven was maintained at 70° C. for 2 min, increased at a rate of 25° C./min to 170° C.

Figure 3A:
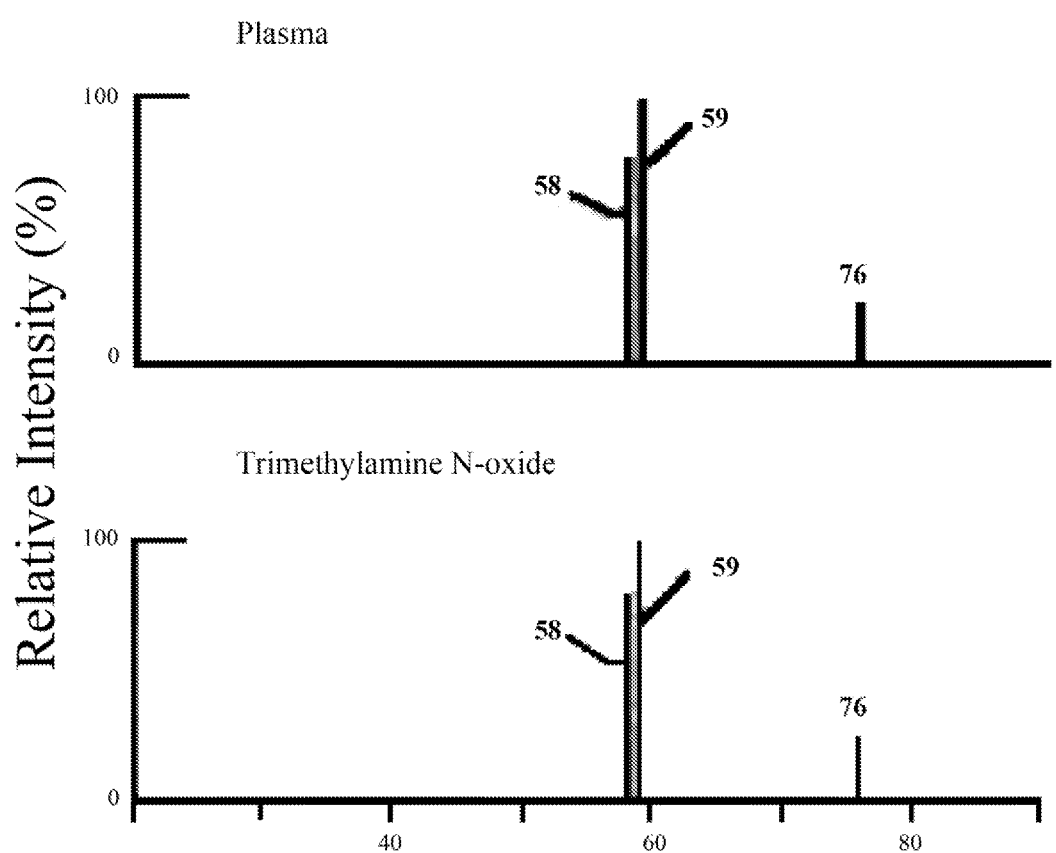
FIG. 3 (panel a) provides collision (energy 21 eV)-induced dissociation (CID) mass spectra corresponding to the peak of m/z=76 in extracted ion chromatogram in positive MS1 mode. Panel (b) provides extracted ion chromatograms in positive-ion multiple reaction monitoring (MRM) mode with parent-to-daughter transition of 76→58. Panel c provides extracted ion chromatograms in positive MRM mode with parent-to-daughter transition of 76→8 except 76→69 for glycine.
Figure 3:
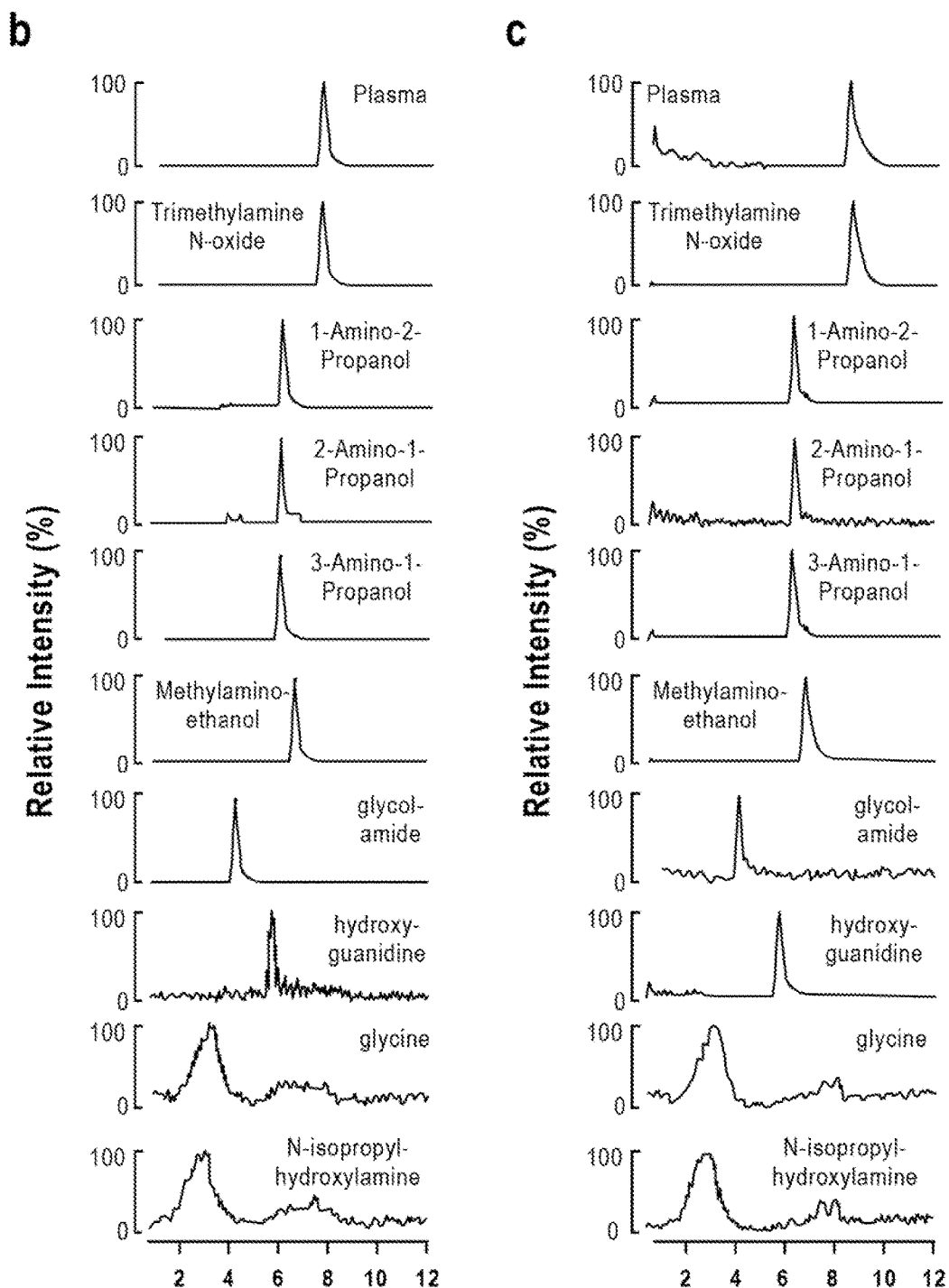

FIG. 3 provides illustrative data confirming that TMANO is identical to the plasma component with m/z 76 that predicts incident CVD risks. Panel a shows the CID spectrum of the plasma component and TMANO are identical. Panels b and c show that the retention time of characteristic parent->daughter ion transitions for the plasma component are identical to TMANO in two distinct HPLC chromatographic systems, and that the other species in plasma with identical molecular weight can be distinguished from TMANO and do not share all properties with the isolated plasma component.

The data provided in FIG. 3(a) was obtained using collision (energy 21 eV)-induced dissociation (CID) mass spectra corresponding to the peak of m/z=76 in extracted ion chromatogram in positive MS1 mode in plasma supernatant and TMANO standard. The data provided in FIG. 3(b) was obtained by extracted ion chromatograms in positive-ion multiple reaction monitoring (MRM) mode with parent-to-daughter transition of 76→58. Sample (20 µl) was injected onto a Phenyl column (4.6×250 mm, 5 pm Rexchrom Phenyl) (Regis) at a flow rate of 0.8 ml/min. The separation was performed using a gradient starting from 10 mM ammonium formate over 0.5 min, then to 5 mM ammonium formate, 25% methanol and 0.1% formic acid over 3 min, held for 8 mm, followed by 100% methanol and water washing for 3 min each. The data provided in FIG. 3(c) was obtained by extracted ion chromatograms in positive MRM mode with parent-to-daughter transition of 76→58 except 76→459 for glycine. Sample (20 pl) was injected onto a Phenyl column (4.6×250 mm, 5 Rexchrom Phenyl) (Regis) at a flow rate of 0.8 ml/min. The separation was performed using a gradient starting from 0.1% formic acid over 2 min, then to 18% acetonitrile with 0.1% formic acid over 18 min, followed by 100% acetonitrile and water washing for 6 min each.

Figure 4:
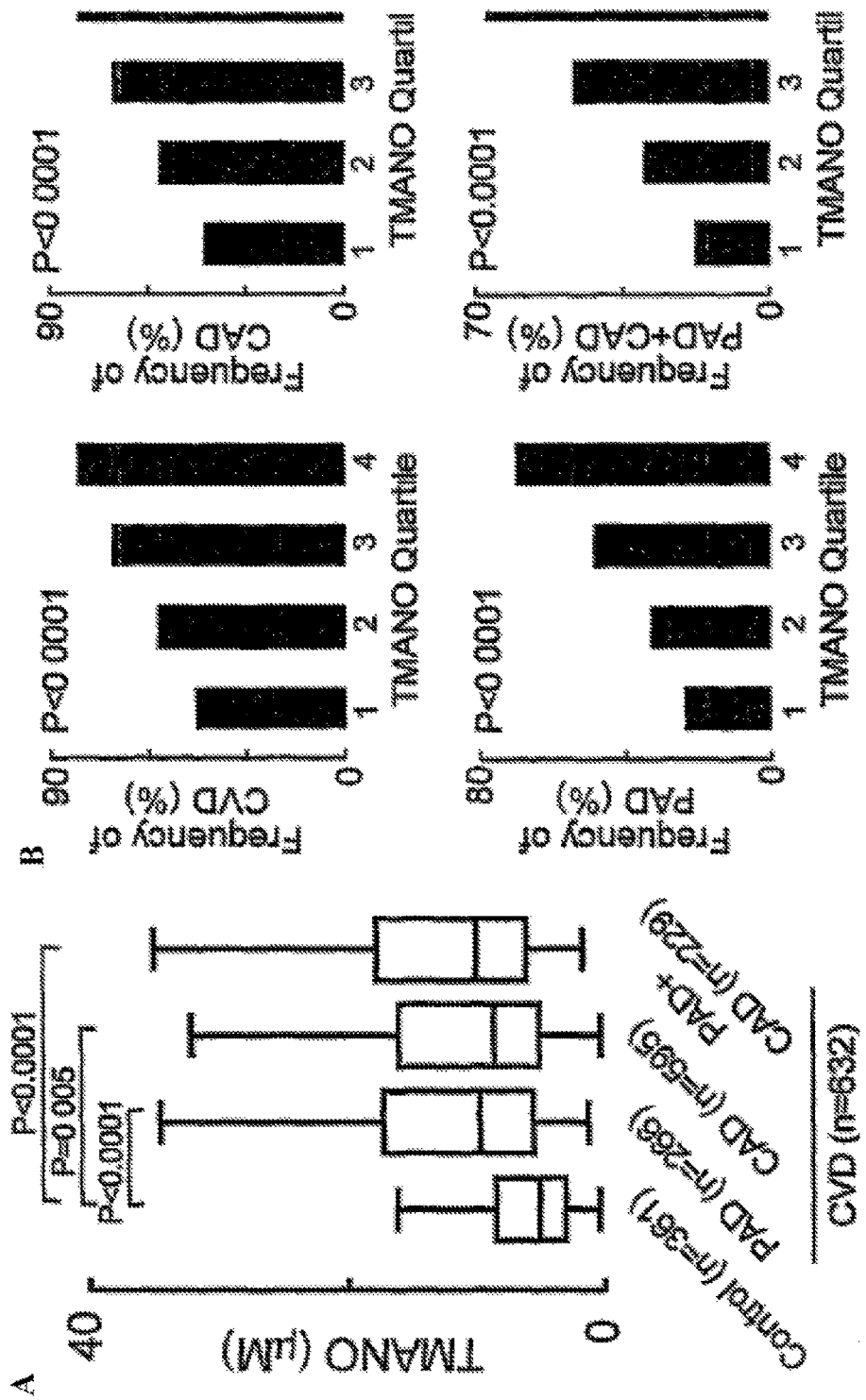
FIG. 4 panels (a-c) provide the results of a case/control study examining the relationship between plasma concentrations of TMANO and the prevalence of atherosclerotic CVD. Plasma was isolated from sequential subjects undergoing diagnostic cardiac catheterization with CVD (n=632) and from control subjects (n=361). Panel (a) shows plasma TMANO in subjects with (n=632) and without (n=361) atherosclerotic CVD. Panel (b) shows the frequency of atherosclerotic CVD, coronary artery disease (CAD) and peripheral artery disease (PAD) according to quartiles of TMANO. P values indicated are for trend across quartiles. Panel (c) shows odds ratio and 95% confidence interval for TMANO levels as a predictor for CVD, CAD, PAD and CAD+PAD risks following multilogistic regression. The model consisted of Framingham risk score, estimated glomerular filtration rate determined by the MDRD formula, C-reactive protein (CRP) and TMANO levels.
Figure 4C:
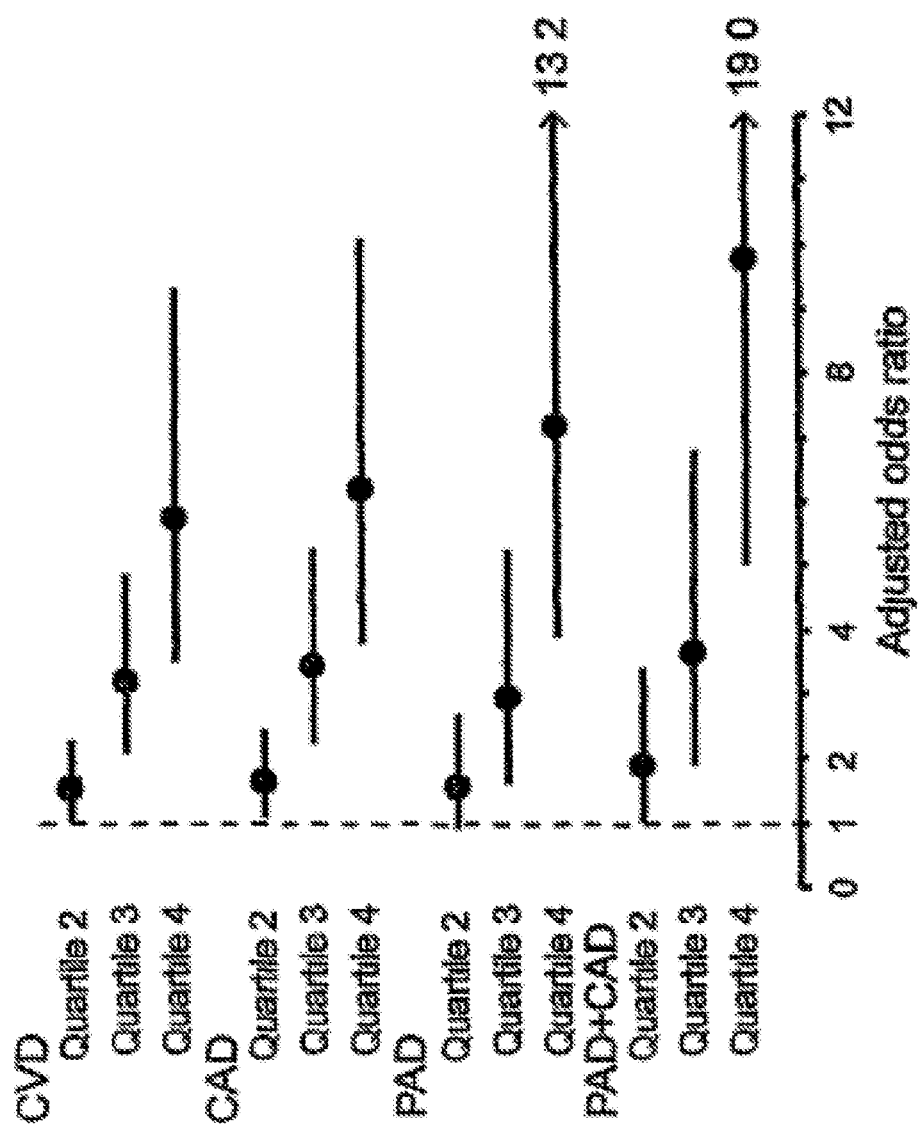

Shown in FIG. 4 and Tables 2a and 2b are results of the first independent clinical validation study to show TMANO predicts risk of having CVD, CAD, PAD or the combination of CAD and PAD amongst approximately 500 sequential men and 500 sequential women undergoing diagnostic cardiac catheterization. Table 2a shows the patient characteristics and demographics of the subjects with CVD versus those without clinical or angiographic evidence of cardiovascular disease. FIG. 4a is a box whisker plot of the levels of TMANO amongst those with CVD versus those without CVD in the study cohort. FIG. 4b shows frequency plots of TMANO levels stratified by quartile of the entire population versus the likelihood of having CVD, CAD, PAD or CAD+PAD for the population. Note that increasing levels of TMANO strongly associate with increased chance of having CVD, CAD, PAD or CAD+PAD. FIG. 4c and Table 2b show the odds ratio and 95% confidence intervals for TMANO levels versus having CVD, CAD, PAD or CAD+PAD following adjustments for traditional cardiac risk factors. These results show measurement of TMANO levels in a large clinical study identify individuals who have risk for having CVD, CAD, PAD or CAD+PAD.

TABLE 2a

Demographics of CVD prevalence

| Characteristic | Controls (n = 361) | Patients with CVD (n = 632) | P value |
|---|---|---|---|
| Age, mean (SD), y | 61.1 (7.8) | 65.4 (9.8) | <0.001 |
| Women, % | 52.4 | 52.1 | 0.98 |
| Diabetes, % | 14.0 | 41.3 | <0.001 |
| Hypertension, % | 28.2 | 37.5 | 0.25 |

TABLE 2a-continued

Demographics of CVD prevalence

| Characteristic | Controls (n = 361) | Patients with CVD (n = 632) | P value |
|---|---|---|---|
| History of smoking, % | 52.4 | 56.0 | 0.73 |
| Current smoking, % | 4.8 | 5.7 | 0.80 |
| LDL cholesterol, median (IQR), mg/dL | 108 (85-130) | 95 (77-122) | <0.001 |
| HDL cholesterol, median (IQR), mg/dL | 49 (40-63) | 42 (35-53) | <0.001 |
| Triglycerides, median (IQR), mg/dL | 115 (82-165) | 139 (103-201) | <0.001 |
| CRP, median (IQR), mg/dL | 1.6 (0.8-3.9) | 3.1 (1.1-7.7) | <0.001 |
| Framingham Risk Score, mean (SD) | 13.3 (3.1) | 14.6 (3.6) | <0.001 |
| MDRD (GFR), mean (SD) | 87.6 (27.2) | 81.9 (50.7) | 0.05 |
| Medication | | | |
| ACEI, % | 33.0 | 54.6 | <0.001 |
| Statin, % | 28.0 | 63.4 | <0.001 |
| Aspirin, % | 54.6 | 75.0 | <0.001 |

TABLE 2b

Odds ratio (95% CI) of cardiovascular disease (CVD) risk according to quartiles of TMANO

| | Quartile TMANO (μM) | | | |
|---|---|---|---|---|
| | 1 (≤4.1) | 2 (4.1-7.0) | 3 (7.0-12.4) | 4 (≥12.4) |
| PAD, Cases (n = 266), Controls (n = 361) | | | | |
| Unadjusted | 1.0 | 157 (0.98-2.54) | 3.01 (1.87-4.87) | 7.39 (4.53-12.06) |
| Model α | 1.0 | 1.56 (0.91-2.67) | 2.94 (1.64-5.26) | 7.18 (3.90-13.22) |
| CAD, Cases (n = 595), Controls (n = 361) | | | | |
| Unadjusted | 1.0 | 1.70 (1.19-2.45) | 3.23 (2.21-4.71) | 5.62 (3.72-8.49) |
| Model α | 1.0 | 1.62 (1.09-2.42) | 3.42 (2.22-5.27) | 6.16 (3.76-10.09) |
| PAD + CAD, Cases (n = 229), Controls (n = 361) | | | | |
| Unadjusted | 1.0 | 1.97 (1.16-3.35) | 4.04 (2.39-6.83) | 9.48 (5.56-16.18) |
| Model α | 1.0 | 1.87 (1.03-3.38) | 3.62 (1.92-6.81) | 9.77 (5.02-19.00) |
| CVD, Cases (n = 632), Controls (n = 361) | | | | |
| Unadjusted | 1.0 | 1.59 (1.11-2.26) | 2.94 (2.03-4.26) | 5.29 (3.52-7.93) |
| Model α | 1.0 | 1.53 (1.04-2.27) | 3.18 (2.08-4.87) | 5.72 (3.51-9.31) |

Figure 5B:
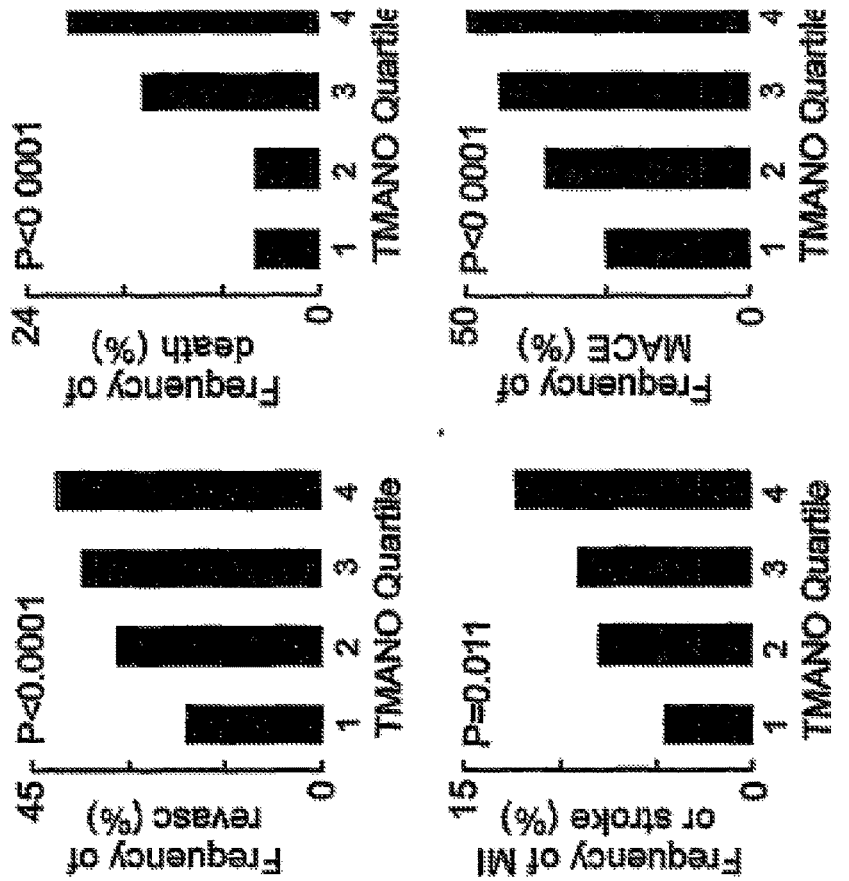
FIG. 5 (a-c) provides the results of a case/control study examining the relationship between plasma abundance of TMANO and prospective risk for major adverse cardiac event (MACE; one or more of the following conditions: non-fatal MI, stroke, need for revascularization (revascularization) or death). Panel (a) shows plasma TMANO in subjects who did (n=374) and did not (n=619) experience subsequent clinical events. Panel (b) shows frequency of clinical events (revascularization, MI or stroke, death, and the composite, MACE) according to quartiles of TMANO abundance. P values indicated are for the trend across quartiles. Panel (c) shows odds ratio and 95% confidence interval versus TMANO quartiles for incident risk of clinical events (need for revascularization, nonfatal MI or stroke, death or the composite, MACE) following multilogistic regression. The model consisted of Framingham risk score, estimated glomerular filtration rate by MDRD formula, C-reactive protein (CRP) and TMANO.
Figure 5A:
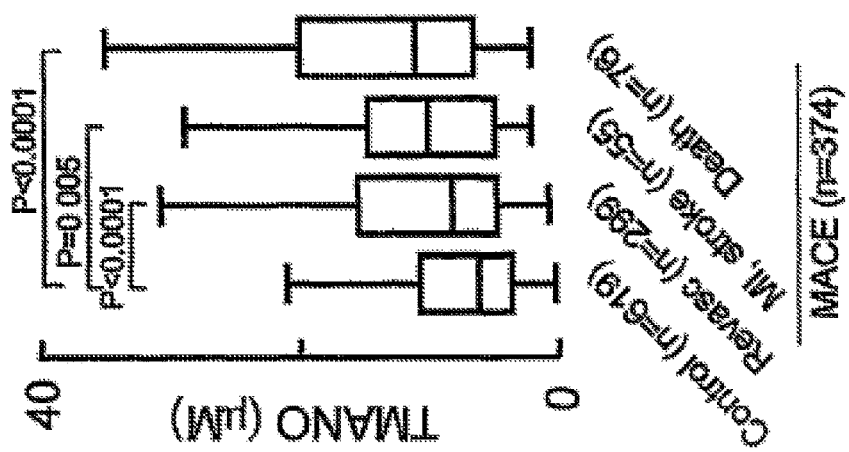
Figure 5C:
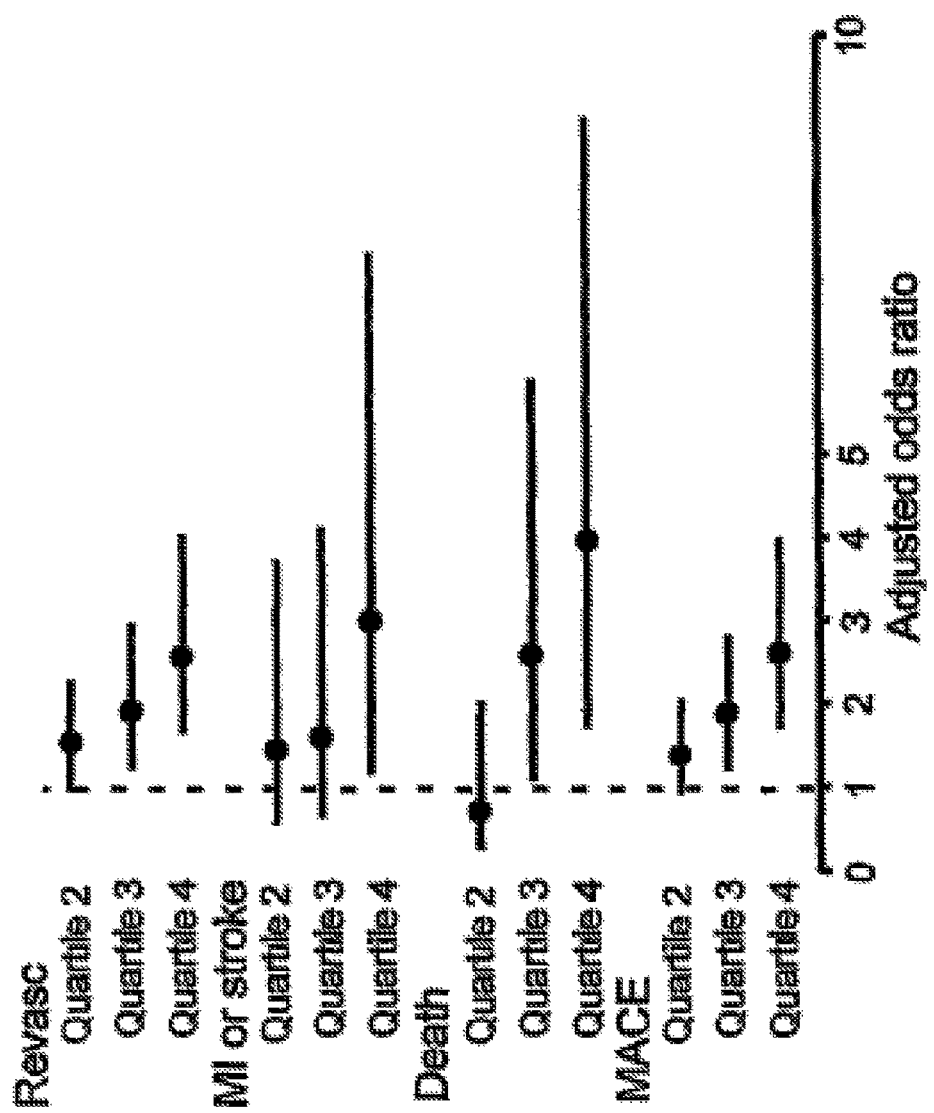

Shown in FIG. 5 and Tables 3a and 3b are the results of a second clinical validation study showing that TMANO levels predict incident 3 year risks of experiencing a nonfatal MI or stroke, a revascularization event, death, or the composite (MACE, major adverse cardiac event) amongst approximately 500 sequential men and 500 sequential women undergoing diagnostic cardiac catheterization. Table 3a shows the patient characteristics and demographics of the subjects stratified by those who experience a MACE over the ensuing 3 yr period following enrollment versus those without MACE. FIG. 5a is a box whisker plot of the levels of TMANO amongst those who experience future MACE versus those who don't in the study cohort. FIG. 5b shows frequency plots of TMANO levels stratified by quartile of the entire population versus the likelihood of experiencing an incident non-fatal MI or stroke, revascularization event (CABG, angioplasty or stent), death, or the composite (MACE) for the entire population. Note that increasing levels of TMANO strongly predict incident 3 year risk for non-fatal MI or stroke, revascularization event (CABG, angioplasty or stent), death, or the composite (MACE). FIG. 5c and Table 3b show the odds ratio and 95% confidence intervals for TMANO levels versus the incident 3 year risk for non-fatal MI or stroke, revascularization event (CABG, angioplasty or stent), death, or the composite (MACE) following adjustments for traditional cardiac risk factors. These results show measurement of TMANO levels serves as a strong and independent predictor of incident 3 year risk for non-fatal MI or stroke, revascularization event (CABG, angioplasty or stent), death, or the composite (MACE).

TABLE 3a

Demographics of subjects with future risk of MACE (Revasculation, MI, stroke, or death)

| Characteristic | Patients without MACE (n = 619) | Patients with MACE (n = 374) | P value |
|---|---|---|---|
| Age, mean (SD), y | 62.8 (8.9) | 65.7 (9.7) | <0.001 |
| Women, % | 50.6 | 54.0 | 0.50 |
| Diabetes, % | 23.4 | 44.9 | <0.001 |

TABLE 3a-continued

Demographics of subjects with future risk of MACE (Revasculation, MI, stroke, or death)

| Characteristic | Patients without MACE (n = 619) | Patients with MACE (n = 374) | P value |
|---|---|---|---|
| Hypertension, % | 68.5 | 84.5 | <0.001 |
| History of smoking, % | 54.9 | 54.8 | 0.98 |
| Current smoking, % | 5.8 | 4.5 | 0.53 |
| LDL cholesterol, median (IQR), mg/dL | 103 (82-128) | 94 (76-122) | 0.005 |
| HDL cholesterol, median (IQR), mg/dL | 47 (37-58) | 41 (34-52) | <0.001 |
| Triglycerides, median (IQR), mg/dL | 127 (92-185) | 140 (103-201) | <0.001 |
| CRP, median (IQR), mg/dL | 2.7 (1.3-6.1) | 3.1 (1.4-6.8) | 0.14 |
| Framingham Risk Score, mean (SD) | 13.7 (3.4) | 14.8 (3.5) | <0.001 |
| MDRD (GFR), mean (SD) | 88.3 (47.8) | 79.1 (35.8) | 0.0002 |
| Medication | | | |
| ACEI, % | 40.5 | 57.0 | 0.001 |
| Statin, % | 43.1 | 65.8 | <0.001 |
| Aspirin, % | 61.9 | 77.0 | <0.001 |

TABLE 3b

Odds ratio (95% CI) of incident risk for MACE (revasculation (Revasc), non-fatal MI, stroke or death) according to quartiles of TMANO

| | Quartile TMANO (µM) | | | |
|---|---|---|---|---|
| | 1 (≤4.1) | 2 (4.1-7.0) | 3 (7.0-12.4) | 4 (≥12.4) |
| | Revasc, Cases (299), Controls (n = 619) | | | |
| Unadjusted | 1.0 | 1.74 (1.15-2.64) | 2.21 (1.47-3.34) | 2.61 (1.73-3.94) |
| Model ζ | 1.0 | 1.49 (0.96-2.31) | 1.89 (1.21-2.96) | 2.57 (1.64-4.02) |
| | Non-fatal MI or stroke, Cases (55), Controls (n = 619) | | | |
| Unadjusted | 1.0 | 1.81 (0.76-4.29) | 2.05 (0.86-4.87) | 2.90 (1.26-6.66) |
| Model ζ | 1.0 | 1.43 (0.55-3.72) | 1.59 (0.62-4.10) | 2.93 (1.16-7.42) |
| | Death, Cases (76), Controls (n = 619) | | | |
| Unadjusted | 1.0 | 1.05 (0.42-2.64) | 3.16 (1.46-6.82) | 4.78 (2.28-10.05) |
| Model ζ | 1.0 | 0.72 (0.26-2.04) | 2.55 (1.10-5.90) | 3.93 (1.71-9.03) |
| | MACE, (Revasc, MI, stroke, or death), Cases (n = 374), Controls (n = 619) | | | |
| Unadjusted | 1.0 | 1.63 (1.11-2.40) | 2.25 (1.54-3.30) | 2.78 (1.90-4.07) |
| Model ζ | 1.0 | 1.37 (0.91-2.08) | 1.86 (1.22-2.83) | 2.62 (1.72-3.99) |

ζ Model consisted of Framingham risk score, MDRD, CRP and TMANO

To obtain the data shown in FIG. 5 plasma was analyzed for TMANO content from case subjects (n=374) who underwent diagnostic cardiac catheterization and experienced MACE in the 3-year period after study enrollment. Parallel analyses were also performed on plasma from control subjects (n=619) who underwent diagnostic cardiac catheterization and did not experience MACE over the 3 years after study enrollment.

Example 2

Using a sequential case:control design, metabolomics analyses (i.e., systematic study of the unique chemical fingerprints left behind by specific cellular processes) were performed by LC/MS to identify small molecules in plasma that identify subjects at risk for MACE over the ensuing 3 year period. Only 13 analytes met the acceptability criterion for discriminating risk in both learning and validation cohorts. Of these metabolites, regression analysis revealed three analytes (with mass-to-charge ratios (m/z) of 76, 104 and 118) were strongly correlated (P<0.0001), suggesting their connection via a common pathway. Using LC/MS/MS, chemical derivatization, GC/MS and feeding of mice with various choline isotopomers, the species with m/z=76, 104 and 118 were unambiguously identified as trimethylamine N-oxide (TMANO), choline and betaine, respectively. Prognostic utility of plasma TMANO, choline and betaine levels for prediction of 3 year MACE risk was confirmed in 1,020 sequential consenting subjects undergoing diagnostic left heart catheterization. Compared to the lowest quartile, subjects with high (4$^{th}$ quartile) levels of either TMANO, choline or betaine were >3-fold more likely to have CAD, >5.0-fold more likely to have PAD, and >2-fold more likely to experience a MACE over the ensuing 3 years independent of Framingham risk factors and CRP.

Example 3

Plasma levels of trimethylamine-N-oxide (TMANO) can be shown to be elevated in patients diagnosed with chronic congestive heart failure. Blood samples from patients with known diagnoses of heart failure (HF) and stable conditions, and control patients without documented signs or symptoms of heart failure or cardiac dysfunction (non-HF), are obtained. Control patients can include other conditions such as diabetes mellitus, hypertension, and chronic obstructive pulmonary disease. The left ventricular ejection fraction is determined by transthoracic echocardiography using Simpson's rule.

Samples are collected using ethylenediamenetetraacetic acid-plasma Vacutainers (Becton Dickinson and Company, Franklin Lakes, N.J.), processed, and frozen at −80° C. until analyzed. Plasma TMANO levels are determined as described in Example 1. Plasma B-type natriuretic peptide (BNP) levels may also be determined by a laboratory based assay (AxSYM BNP, Abbott Diagnostics, Inc., Abbott Park, Ill.). The Kruskal-Wallis (rank-sum) test is used to compare differences in TMANO and BNP grouped according to HF cohorts and across New York Heart Association (NYHA) classes. Analysis of variance tests assess differences in continuous clinical variables across TMANO quartiles, whereas the Cochran-Armitage test detects trends in proportions of patients with HF, ischemic cause, or male gender across TMANO quartiles. Natural logarithmic transformations are applied for determining Spearman's correlation coefficients. The odds ratio of having HF is calculated from multivariate logistic regression across the second, third, and fourth quartiles of TMANO with respect to the first quartile (odds ratio 1.0). Adjustments may be made for age and BNP levels. Receiver-operating characteristic analysis calculates the optimal TMANO cutoffs for predicting HF. A p value <0.05 is considered statistically significant. Statistical analysis is performed using JMP 5.1 (SAS Institute Inc., Cary, N.C.).

Results are expected to show increasing quartiles of TMANO levels are associated with a greater prevalence of HF.

The mean plasma TMANO levels in the HF cohort are expected to be significantly elevated compared with those of control patients. Furthermore, the mean plasma TMANO levels are expected to increase in parallel with increasing NYHA class.

This study will demonstrate that plasma TMANO levels are elevated in patients with HF, with increasing levels associated with worsening NYHA class.

Example 4

Plasma levels of TMANO can be shown to have prognostic value in evaluating patients with chronic heart failure. The primary objective of this study is to determine the relationship between plasma TMANO levels and cardiac structure, systolic and diastolic performance, and overall prognosis in patients with chronic systolic HF.

The neurohormonal sub-study of the ADEPT (assessment of Doppler Echocardiography in Prognosis and Therapy) study has been previously described. See Troughton et al., J. Am. Coll. Cardiol. 43, 416-22 (2004). Patients with stable, chronic systolic heart failure (HF) (Left ventricular ejection fraction [LVEF]≤35%, New York Heart Association functional class II to IV) undergo echocardiographic evaluation of systolic and diastolic performance as well as plasma sample collection. Clinical events (all-cause mortality, cardiac transplantation, or HF hospitalization) are tracked by scheduled telephone follow-up and validated by chart review as described by Troughton et al. (Am. J. Cardiol 96, 257-62 (2005)). Creatinine clearance may be calculated using the Crockcroft-Gault equation based on creatinine, age, and weight. Plasma B-type natriuretic peptide (BNP) levels may be analyzed by the Christchurch BNP assay.

Samples are collected using ethylenediaminetetraacetic acid plasma tubes, processed and frozen at −80° C. until analyzed. Plasma TMANO levels are determined as described in Example 1. Laboratory analyses should be performed with investigators blind to the clinical outcomes.

Comprehensive transthoracic echocardiography can be performed using commercially available HDI 5000 (Phillips Medical Systems, Bothell, Wash.) and Acuson *Sequoia* (Siemens Medical Solutions USA, Inc., Malvern, Pa.) machines. Two-dimensional and color Doppler imaging can be performed in standard parasternal and apical views. Diastolic indexes (including pulse-wave Doppler, color M-mode, and tissue Doppler imaging) are acquired over 10 consecutive beats using sweep speeds of 50 cm/s and 100 cm/s using previously described techniques. Classification of diastolic stage is determined as follows: Stage I (impaired relaxation) consists of mitral E/A<1, deceleration time>220 ms, pulmonary vein S/D>1, atrial reversal (AR)<35 cm/s; Stage II (pseudonormal) shows mitral E/A=1 to 2, pulmonary vein S/D<1, deceleration time<220 ms, AR ?35 cm/s; Stage III (restrictive) gives mitral ENp ratios. The LVEF and cardiac volumes are measured using the Simpson biplane method. Measurements are averaged over 3 cycles (5 cycles for atrial fibrillation), and 2 experienced individuals who are blind to the neurohormonal data make all measurements.

Plasma TMANO levels may be non-normally distributed and treated as nonparametric variables (expressed as median and interquartile range [IQR]). Analysis of variance or the Kruskal-Wallis test is used to assess differences in continuous clinical variables across TMANO tertiles according to whether or not the distribution is normal, whereas contingency table analysis is performed to assess differences in clinical proportions across TMANO tertiles. Normality is assessed by the Shapiro-Wilk W test. The Spearman rank correlation method is used as a nonparametric measure of association for correlations between plasma TMANO levels and all clinical variables. The odds ratios of having altered systolic or diastolic performances are calculated from multivariate logistic regression across 1st, 2nd, and 3rd tertiles of TMANO with respect to the 1st tertile (odds ratio=1.0). Adjustments can be made for age and BNP levels. Kaplan-Meier survival plots can be calculated from baseline to time of all-cause mortality, cardiac transplantation, or HF hospitalization over a mean follow-up of 33 months. All univariate and multivariate Cox proportionality hazard analyses are also calculated with all-cause mortality, cardiac transplantation, or HF hospitalization as outcome, and with plasma TMANO levels treated as a categorical variable modeling differences in outcomes for patients within the highest 2 tertiles relative to the lowest of plasma TMANO. Receiver-operator characteristic curve analysis can be performed to determine the incremental prognostic value of TMANO with BNP. A p value <0.05 is considered statistically significant. Statistical analyses are performed using SAS version 9.1 and JMP version 5.1 (SAS Institute Inc., Cary, N.C.).

It is expected that increasing plasma TMANO levels will be associated with a higher proportion of right ventricular systolic dysfunction. In multivariable stepwise logistic regression analysis using variables that show statistically significant correlation with logarithmic transformed plasma TMANO levels, only tissue Doppler imaging-derived septal Aa wave is expected to show an independent association with TMANO levels.

Patients with an elevated level of one or more choline-related trimethylamine-containing compounds can be expected to experience a cardiovascular event, death or cardiac transplantation.

Example 5

TMANO levels in healthy elderly subjects can also be used to predict risk for developing heart failure. The goal of the present study is to assess the risk for incident HF; therefore, patients will be excluded if they had prevalent HF, prevalent myocardial infarction (MI), prevalent stroke, or died prior to the initial visit. Follow-up for events will continue. Factors assessed during the initial exam may include age, race, gender, diabetes, hypertension, smoking, sub-clinical vascular disease, alcohol use, current medications, height, weight, blood pressure and laboratory measurements (TMANO and lipids) and are included as covariates in multivariable analysis. For the diagnosis of prevalent heart failure, self-reports are confirmed by components of a physical exam, or if necessary, by a validation protocol that includes surveys of treating physicians or review of medical records. For the diagnosis of incident heart failure, a physician's diagnosis of heart failure will be followed by a review of the participant's medical records. The incidence of heart failure is then determined by a committee based on diagnosis from a physician, as well as consideration of symptoms, signs, chest X-ray findings, and treatment of heart failure (current prescription for diuretic agent and either digitalis or vasodilator). Systolic and diastolic blood pressures are calculated from the mean of two consecutive readings in the seated position. Smoking is defined as current versus not. Low-density lipoprotein (LDL) cholesterol can be calculated by the Friedewald formula. Subclinical cardiovascular diseases (CVD) documented may include abnormalities in carotid intima-media thickness as monitored by ultrasound, ankle-arm index, elevated left ventricular mass by electrocardiography, and major electrocardiographic abnormalities. Follow-up interviews for events (including MI and stroke) may occur every 6 months and in person annually.

Trimethylamine-N-oxide (TMANO) is measured from frozen samples collected at the initial exam. Plasma TMANO levels are determined using the method described in Example 1.

A pre-specified statistical analysis plan is performed including quartile based analysis and comparisons made of the distribution of demographic characteristics and traditional cardiovascular risk factors across the quartile groups. Differences in baseline characteristics are compared using the Cochrane-Armitage trend test for continuous variables and Chi Square tests for categorical variables. The association between TMANO and HF is determined with multivariate Cox proportional hazards regression models. To evaluate the contribution of TMANO quartiles as a marker of risk, models are generated in stages: unadjusted; then adjusted for demographics and cardiovascular risk factors. Analysis is performed with a time-dependent variable for incident MI added to the model to evaluate the effect of controlling for this intervening event on the association of baseline characteristics censoring for participants with incident MI.

It is expected that higher levels of TMANO will be associated with higher incident HF.

The inventors have developed two multivariate models which can be used to explore the interaction between TMANO levels in blood and traditional cardiac risk factors and myocardial infarction. In model 1, the inventors treat MI as a time-dependent covariate. After adjusting for age, gender, systolic blood pressure (SBP), smoking, low-density lipoprotein (LDL) cholesterol, diabetes mellitus, any subclinical cardiovascular disease and MI as a time-dependent covariate, it is expected that elevated TMANO levels will predict subjects at increased risk for developing incident HF.

Example 6

TMANO levels in patients can also be used to predict risk for developing aortic disorders such as aortic dissection or aortic aneurysms. Patients will be excluded if they previously exhibited an aortic disorder such as aortic dissection or aortic aneurysm. Other factors that may be assessed during the initial exam include age, race, gender, diabetes, hypertension, smoking, sub-clinical vascular disease, alcohol use, current medications, height, weight, blood pressure and laboratory measurements (TMANO and lipids) and are included as covariates in multivariable analysis. For the diagnosis of an aortic disorder such as aortic dissection or aortic aneurysm, reports are confirmed by a physical exam or a review of medical records. Preferably the aortic disorder is confirmed using diagnostic imaging technology. Follow-up interviews or examination for aortic disorders (including aortic dissection and/or aortic aneurysm) may occur every 3 months, every 6 months, annually, or using other schedules.

To correlate Trimethylamine-N-oxide (TMANO) levels with the development of aortic disorders, the level of TMANO is first measured from frozen samples collected at the initial exam. Plasma TMANO levels are determined using the method described in Example 1. Patients are then evaluated at 3 month, 6 month, 1 year, or another interval such as 2 or 3 years to identify the number of patients who have experienced or are experiencing an aortic disorder. The number of aortic dissections and aortic aneurysms may be separately tabulated.

A pre-specified statistical analysis plan is performed including quartile based analysis and comparisons made of the distribution of demographic characteristics and traditional cardiovascular risk factors across the quartile groups. Differences in baseline characteristics are compared using the Cochrane-Armitage trend test for continuous variables and Chi Square tests for categorical variables. The association between TMANO and aortic disorders is determined with multivariate Cox proportional hazards regression models. To evaluate the contribution of TMANO quartiles as a marker of risk, models are generated in stages: unadjusted; then adjusted for demographics and cardiovascular risk factors.

It is expected that higher levels of TMANO will be associated with higher incidence of aortic disorders such as aortic dissection and aortic aneurysm. In addition, multivariate models can be used to explore the interaction between TMANO levels in blood and traditional cardiac risk factors. In multivariate models, after adjusting for age, gender, systolic blood pressure (SBP), smoking, low-density lipoprotein (LDL) cholesterol, diabetes mellitus, any sub-clinical cardiovascular disease and MI as a time-dependent covariate, it is expected that elevated TMANO levels will predict subjects at increased risk for developing aortic disorders such as aortic dissection and/or aortic aneurysm.

Example 7

This Example describes the prognostic value of trimethylamine species TMANO, choline, and betaine. Subjects included in analyses were enrolled in the ADEPT trial, which examined long term outcomes in subjects with systolic or diastolic heart failure. The results, presented below in Table 4, show that TMANO, choline and betaine are associated with risks for death and death following heart transplantation, and for choline and betaine, risk for unscheduled hospitalizations for heart failure. It is noted that TMANO trends the same way but fails to reach significance as a continuous variable because of inadequate sample number in this Example. If looking at 4th vs 1st quartile levels of TMANO, there is a significant (p<0.05) association of high TMANO level with unscheduled hospitalizations as well.

below median value of plasma TMANO among CHF subjects only is shown below (stratified across median of 5.21 within this group). Subsequent analyses also showed that plasma TMANO (r=0.24, p<0.001) and choline (r=0.23, p<0.001) have modest correlations with indices of subclinical myocardial stretch and dysfunction as monitored with plasma BNP.

TABLE 4

| Variable | HR (95% CI) | p-value | Endpoint | # Events |
| --- | --- | --- | --- | --- |
| TMANO (μM) | 1.34 (0.95-1.70) | 0.090 | 3 year - Death | 16 |
| TMANO (μM) | 1.27 (0.94-1.57) | 0.110 | 3 year - Death/tx | 24 |
| TMANO (μM) | 1.16 (0.84-1.45) | 0.318 | 3 year - Death/tx/hosp | 34 |
| TMANO (μM) | 1.39 (1.07-1.70) | 0.018 | 5 year - Death | 33 |
| TMANO (μM) | 1.34 (1.05-1.60) | 0.021 | 5 year - Death/tx | 40 |
| TMANO (μM) | 1.21 (0.94-1.47) | 0.125 | 5 year - Death/tx/hosp | 46 |
| Choline (μM) | 1.73 (1.21-2.31) | 0.004 | 3 year - Death | 16 |
| Choline (μM) | 1.49 (1.09-1.95) | 0.016 | 3 year - Death/tx | 24 |
| Choline (μM) | 1.40 (1.05-1.78) | 0.023 | 3 year - Death/tx/hosp | 34 |
| Choline (μM) | 1.61 (1.23-2.03) | 0.001 | 5 year - Death | 33 |
| Choline (μM) | 1.48 (1.14-1.84) | 0.004 | 5 year - Death/tx | 40 |
| Choline (μM) | 1.36 (1.06-1.69) | 0.018 | 5 year - Death/tx/hosp | 46 |
| Betaine (μM) | 1.51 (0.98-2.20) | 0.063 | 3 year - Death | 16 |
| Betaine (μM) | 1.56 (1.12-2.10) | 0.010 | 3 year - Death/tx | 24 |
| Betaine (μM) | 1.48 (1.10-1.94) | 0.010 | 3 year - Death/tx/hosp | 34 |
| Betaine (μM) | 1.27 (0.91-1.72) | 0.155 | 5 year - Death | 33 |
| Betaine (μM) | 1.39 (1.05-1.79) | 0.024 | 5 year - Death/tx | 40 |
| Betaine (μM) | 1.42 (1.08-1.82) | 0.013 | 5 year - Death/tx/hosp | 46 |
| Ln TMANO (μM) | 1.50 (0.95-2.28) | 0.079 | 3 year - Death | 16 |
| Ln TMANO (μM) | 1.53 (1.06-2.14) | 0.025 | 3 year - Death/tx | 24 |
| Ln TMANO (μM) | 1.19 (0.85-1.63) | 0.308 | 3 year - Death/tx/hosp | 34 |
| Ln TMANO (μM) | 1.41 (1.01-1.94) | 0.046 | 5 year - Death | 33 |
| Ln TMANO (μM) | 1.48 (1.10-1.96) | 0.010 | 5 year - Death/tx | 40 |
| Ln TMANO (μM) | 1.15 (0.85-1.52) | 0.361 | 5 year - Death/tx/hosp | 46 |
| Ln Choline (μM) | 2.21 (1.39-3.46) | <0.001 | 3 year - Death | 16 |
| Ln Choline (μM) | 1.73 (1.18-2.50) | 0.005 | 3 year - Death/tx | 24 |
| Ln Choline (μM) | 1.55 (1.12-2.13) | 0.009 | 3 year - Death/tx/hosp | 34 |
| Ln Choline (μM) | 1.86 (1.33-2.56) | <0.001 | 5 year - Death | 33 |
| Ln Choline (μM) | 1.64 (1.22-2.20) | 0.001 | 5 year - Death/tx | 40 |
| Ln Choline (μM) | 1.46 (1.09-1.93) | 0.010 | 5 year - Death/tx/hosp | 46 |
| Ln Betaine (μM) | 1.67 (1.00-2.78) | 0.049 | 3 year - Death | 16 |
| Ln Betaine (μM) | 1.81 (1.20-2.71) | 0.005 | 3 year - Death/tx | 24 |
| Ln Betaine (μM) | 1.67 (1.18-2.37) | 0.004 | 3 year - Death/tx/hosp | 34 |
| Ln Betaine (μM) | 1.34 (0.94-1.92) | 0.105 | 5 year - Death | 33 |
| Ln Betaine (μM) | 1.51 (1.10-2.08) | 0.011 | 5 year - Death/tx | 40 |
| Ln Betaine (μM) | 1.54 (1.14-2.11) | 0.005 | 5 year - Death/tx/hosp | 46 |

*HRs per 1 SD increments (1 SD TMANO = 20.7 μM; 1 SD Choline = 4.9 μM; 1 SD Betaine = 11.9 μM; 1 SD Ln TMANO = 0.99 μM; 1 SD Ln Choline = 0.38 μM; 1 SD Ln Betaine = 0.27 μM).

Figure 6:
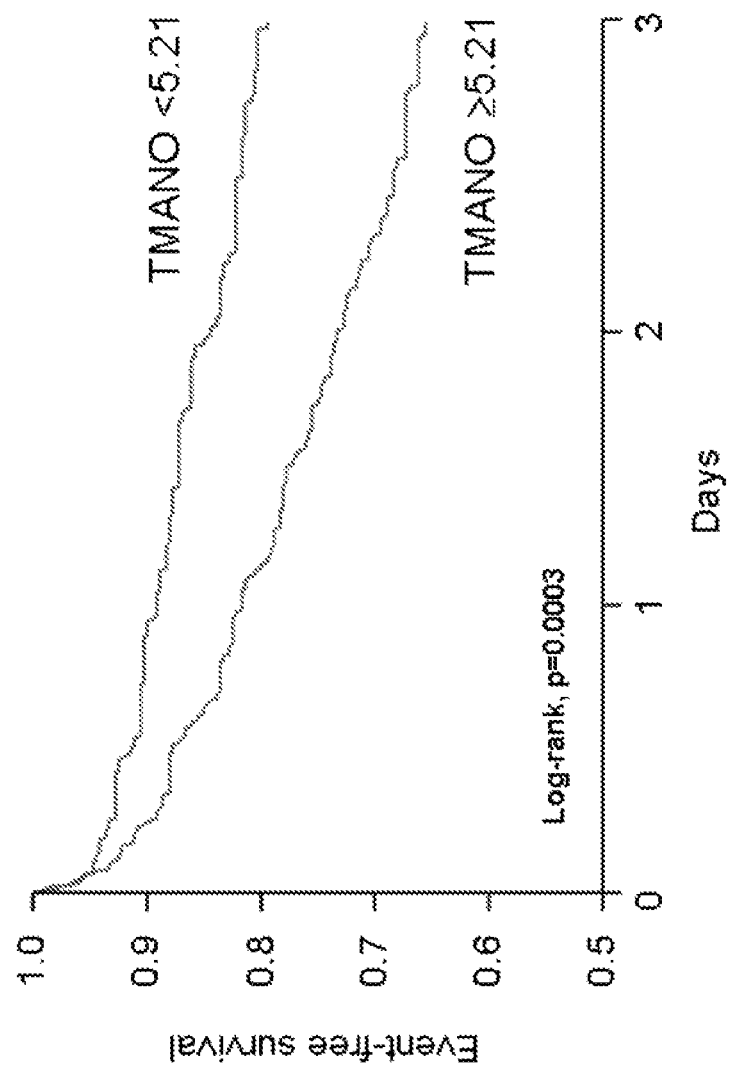
FIG. 6 shows the prognostic value of TMANO in plasma in prediction of heart failure in the cohort described in Example 7.

Plasma TMANO levels were examined among sequential subjects (n=2983) undergoing cardiac evaluation (GeneBank cohort). Overall, patients with left ventricular systolic dysfunction (LVSD) have higher levels of TMANO (p<0.001), consistent with TMANO levels as a marker for HF (heart failure) and LVSD. FIG. 6 looks at the prognostic value of TMANO in prediction of heart failure in the cohort. Of the cohort monitored, approximately 18% had a history of congestive heart failure (CHF, n=537) while the majority had no history of CHF (n=2446). Levels of TMANO were higher in CHF (P<0.001). Among those with CHF, an elevated level of TMANO was observed among those at increased risk for development of non-fatal MI, stroke or death (median 5.21 vs 3.54, HR 1.22, 1.09-1.35, p=0.001). Similar results were seen with alternative trimethylamine species. For example, elevated choline was significantly associated with non-fatal MI, stroke or death among CHF subjects (11.8 vs 10, HR 1.18, 1.06-1.3, p=0.004). Kaplan Meier (KM) survival plot for the relationship of above vs Example 8

This Example provides results demonstrating the prognostic and diagnositc value of crotonobetain (both the cis and trans isomers), gamma-butyrobetaine, and carnitine in cardiovascular disease, stroke, need for revascularization, diabetes mellitus, insulin resistance, metabolic syndrome, non-alcoholic fatty liver disease (NAFLD), and non-alcoholic metabolic syndrome (NASH).

Figure 7C:
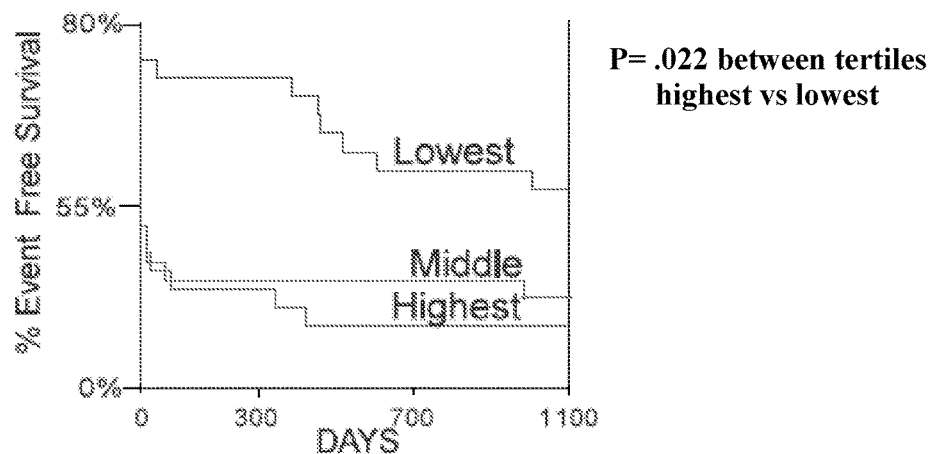
FIG. 7 shows Kaplan Meier plots of tertiles of crotonobetaine (7a), gamma-butyrobetaine (7B), and carnitine (7C) as described in Example 8.

Subjects undergoing cardiac evaluation were consented for blood draw, and plasma isolated and frozen at −80 C until time of analysis. Subjects were monitored over the ensuing 4 years for development of major adverse cardiac events including myocardial infarction (MI), stroke, need for revascularization or death. Plasma was analyzed by stable isotope dilution LC/MS/MS for the indicated trimethyl amine containing species. Shown, in FIG. 7 are the Kaplan Meier survival curves (stratified into tertiles) for the indicated trimethylamine containing analytes versus risk for the composite of death, non-fatal MI or stroke, or need for revascularization. In particular, FIG. 7A shows this data for crotonobetaine, FIG. 7B shows this data for gamma-butyrobetaine, and FIG. 7C shows this data for carnitine.

Figure 8A:
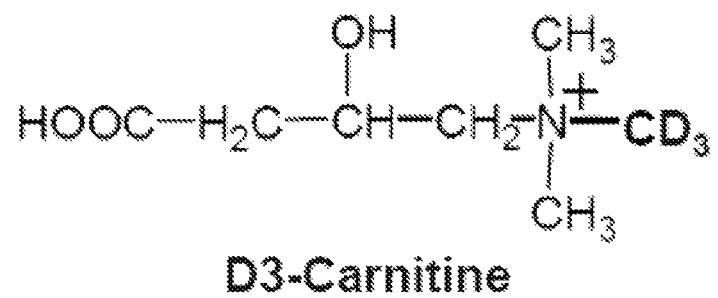
FIG. 8 shows D3-Carnitine (shown in 8A) is metabolized to pro-atherogenic trimethylamine (TMA) (8B) and trimethylamineoxide (TMANO) (8C) in a gut flora dependent pathway.
Figure 8:
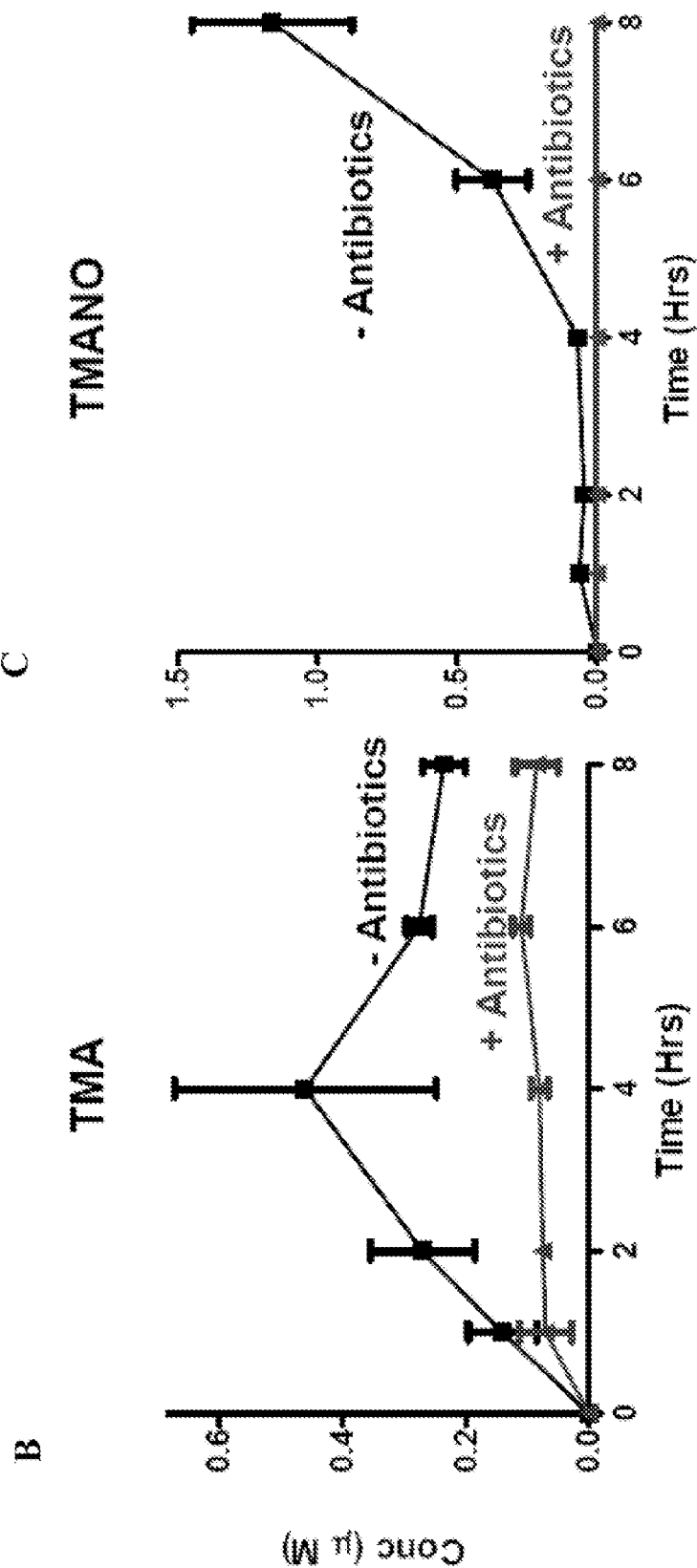

In additional work, mice were gavaged with D3-carnitine and the time dependent appearance of D3-TMA and TMANO were quantified in plasma. Where indicated in FIG. 8, mice were pretreated for 3 weeks with a broad spectrum antibiotic cocktail to suppress intestinal microflora. Note that both TMA and TMANO are generated as a metabolite of carnitine ingestion, and suppression of gut flora dramatically reduces their production. Plasma levels of the deuterium (D3) labeled metabolites of D3-carnitine, D3-TMA and D3-TMANO, were quantified in plasma by stable isotope dilution LC/MS/MS analysis. D3-Carnitine was given by gavage feeding to mice at t=0. Results are shown in FIG. 8, with TMA production shown in FIG. 8B and TMANO production in FIG. 8C.

Figure 9:
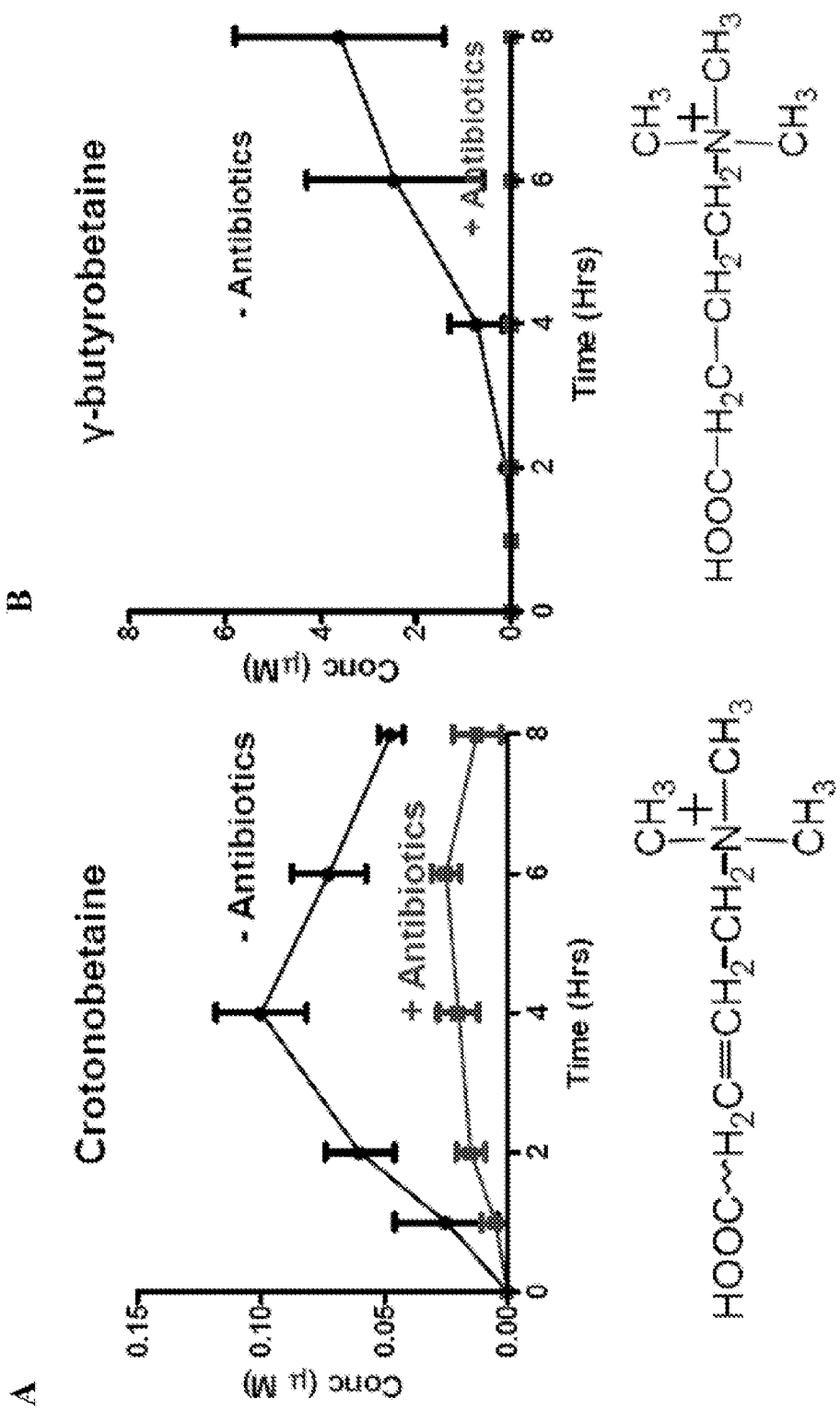
FIG. 9 shows Carnitine is also metabolized to crotonobetaine (9A) and γ-butyrobetaine (9B) by a gut flora dependent process.
Figure 10:
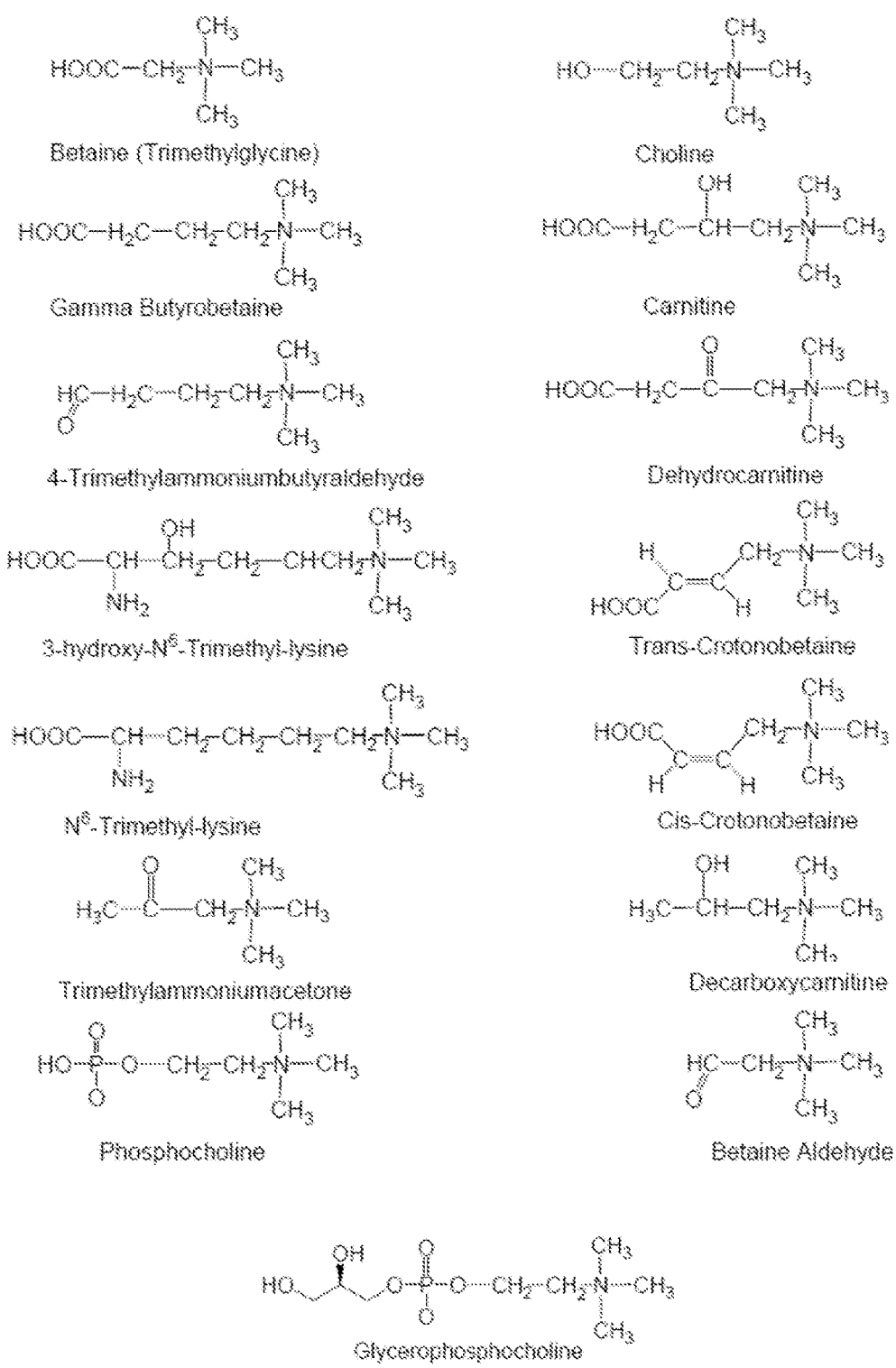
FIG. 10 shows the chemical formula of certain choline-related trimethylamine-containing compounds useful in the present invention.

In further work, mice were gavaged with D3-carnitine and the time dependent appearance of D3-crotonobetaine and gamma butyrobetaine were quantified in plasma. Where indicated in FIG. 9, mice were pretreated for 3 weeks with a broad spectrum antibiotic cocktail to suppress intestinal microflora. Note that both compounds are generated as a metabolite of carnitine ingestion, and suppression of gut flora dramatically reduces their production. D3-crotonobetaine and D3-gamma-butyrobetaine were quantified in plasma by LC/MS/MS analysis isolated at the indicated times following D3-carnitine gavage feeding. Results are shown in FIG. 9, with crotonbetaine production shown in FIG. 9A, and gamma-butyrobetain production shown in FIG. 9B.

In further work, subjects undergoing cardiac evaluation were consented for blood draw, and plasma isolated and frozen at −80 C until time of analysis. Subjects were monitored over the ensuing 4 years for development of major adverse cardiac events including myocardial in MI, stroke, need for revascularization or death. Plasma was analyzed by stable isotope dilution LC/MS/MS for the indicated trimethyl amine containing species. The relationship between plasma levels of the indicated trimethyl amine species and relative risk and 95% confidence intervals for experiencing the composite endpoints of death, non-fatal MI or stroke, or need for revascularization are shown in Table 5. Also shown are adjusted relative risks (95% confidence intervals) for each analyte in multilogistic regression models where adjustments for traditional cardiac risk factors indicated was performed.

TABLE 5

Relative risk over 4 year period of patients experiencing composite events death, MI, stroke, or revascularizaton.

| Unit | Unadjusted | P | Adjusted* | P |
|---|---|---|---|---|
| Crotonobetaine Tertiles (Highest vs Lowest) | 3.2 (1.2-8.1) | .016 | 7.4 (2.1-26) | .002 |
| γ-butyrobetaine Tertiles (Highest vs Lowest) | 2.4 (1.01-5.8) | .047 | 3.0 (.97-9.2) | .056 |
| Carnitine Tertiles (Highest vs Lowest) | 2.3 (1.03-5.0) | .042 | 3.0 (1.7-7.9) | .023 |

*Adjusted for age, sex, Total Cholesterol, Diabetes, Hypertension, Hyperlipidemia, coronary artery disease, smoking history, and BMI Within the same cohort, the prognostic value of crotonobetaine for predicting risk of having diabetes was evaluated. Individuals possessing high (top tertile) plasma level of crotonobetaine were at dramatically increased risk for having type2 diabetes than subjects with plasma levels in the bottom tertile. This association remained true even following adjustments for multiple risk factors, including age, sex, Total Cholesterol, Hypertension, Hyperlipidemia, coronary artery disease, smoking history, and BMI. These results are shown in Table 6.

TABLE 6

Odds of disease prevalence of diabetes mellitus in the highest versus lowest tertile of crotonbetaine.

| Unit | Unadjusted | P | Adjusted* | P |
|---|---|---|---|---|
| Crotonobetaine Tertiles (Highest vs Lowest) | 9.8 (2.6-37.0) | .001 | 19.0 (1.97-183) | .011 |

*Adjusted for age, sex, Total Cholesterol, Hypertension, Hyperlipidemia, coronary artery disease, smoking history, and BMI In the same clinical cohort, plasma levels of fasting insulin and glucose were determined, and the ability of plasma levels of crotonobetaine to predict insulin resistance, as monitored by the glucose/insulin ratio, was examined. Crotonobetaine served as a strong and independent predictor of insulin resistance, even after multilogistic regression analyses for multiple risk factors. These results are shown in Table 7.

TABLE 7

Crotonobetaine predicts risks for insulin resistance (glucose/insulin ratio)

| Unit | Unadjusted | P | Adjusted* | P |
|---|---|---|---|---|
| Crotonobetaine Tertiles (Highest vs Lowest) | 12.1 (3.3-42.7) | <0.001 | 18.4 (2.33-221) | <0.001 |

*Adjusted for age, sex, Total Cholesterol, Hypertension, Hyperlipidemia, coronary artery disease, DM, smoking history, and BMI In the same clinical cohort, plasma levels of fasting insulin, and a complete metabolic panel were determined, and the ability of plasma levels of crotonobetaine to predict insulin resistance, as monitored by the HOMA formula, was examined. Crotonobetaine served as a strong and independent predictor of insulin resistance, even after multilogistic regression analyses for multiple risk factors. These results are shown in Table 8.

TABLE 8

Crotonobetaine predicts risks for insulin resistance (HOMA)

| Unit | Unadjusted | P | Adjusted* | P |
|---|---|---|---|---|
| Crotonobetaine Tertiles (Highest vs Lowest) | 7.5 (1.9-24.4) | 0.001 | 14.5 (2.34-132) | <0.001 |

*Adjusted for age, sex, Total Cholesterol, Hypertension, Hyperlipidemia, coronary artery disease, DM, smoking history, and BMI In the same clinical cohort, plasma levels of fasting insulin, and a complete metabolic panel were determined, and the ability of plasma levels of crotonobetaine to predict insulin resistance, as monitored by the HOMA formula, was examined. Crotonobetaine served as a strong and independent predictor of insulin resistance, even after multilogistic regression analyses for multiple risk factors.

In the same clinical cohort, the ability of plasma levels of crotonobetaine to predict likelihood of the subject having metabolic syndrome was examined. Crotonobetaine served as a strong and independent predictor of metabolic syndrome, even after multilogistic regression analyses for multiple risk factors. These results are shown in Table 9.

TABLE 9

Crotonobetaine predicts risks for Metabolic Syndrome

| Unit | Unadjusted | P | Adjusted* | P |
|---|---|---|---|---|
| Crotonobetaine Tertiles (Highest vs Lowest) | 3.3 (1.2-7.1) | 0.01 | 8.1 (2.4-16.3) | <0.001 |

*Adjusted for age, sex, Total Cholesterol, Hypertension, Hyperlipidemia, coronary artery disease, DM, smoking history, and BMI Subjects (n=50) with diagnosis of NAFLD or NASH based upon medical record were identified within the GeneBank cohort (comprised of sequential subjects undergoing elective diagnostic cardiac catheterization) and age and gender matched subjects without known history of NAFLD or NASH were used as controls (n=50). Fasting plasma level of crotonobetaine was determined by stable isotope dilution, LC/MS/MS analysis. The ability of fasting plasma levels of crotonobetaine to predict likelihood of the subject having NAFLD or NASH were examined. Crotonobetaine is observed to serve as a strong and independent predictor of both NAFLD and NASH, even after multilogistic regression analyses for multiple risk factors. These results are shown in Table 10.

TABLE 10

Crotonobetaine predicts risks for nonalcoholic fatty liver disease (NAFLD) and non-alcoholic metabolic syndrome (NASH)

| Unit | Unadjusted | P | Adjusted* | P |
|---|---|---|---|---|
| NAFLD | | | | |
| Crotonobetaine Tertiles (Highest vs Lowest) | 2.2 (1.1-5.8) | 0.01 | 3.1 (1.7-8.6) | 0.001 |
| NASH | | | | |
| Crotonobetaine Tertiles (Highest vs Lowest) | 1.7 (1.1-4.8) | 0.02 | 1.9 (1.2-5.1) | 0.03 |

*Adjusted for age, sex, ALT, AST, Total Cholesterol, Hypertension, Hyperlipidemia, coronary artery disease, DM, smoking history, and BMI

Example 9

This Example provides results demonstrating that TMA is generated from ingested phosphatidylcholine (PC, timethyl amine containing compound) in a gut flora dependent fashion in humans. TMA is detected in plasma. While TMA is a gas at room and body temperature, if one acidifies the plasma, and the sample flash frozen and analyzed immediately upon thaw, one can measure the TMA cation by mass spectrometry.

Figure 11:
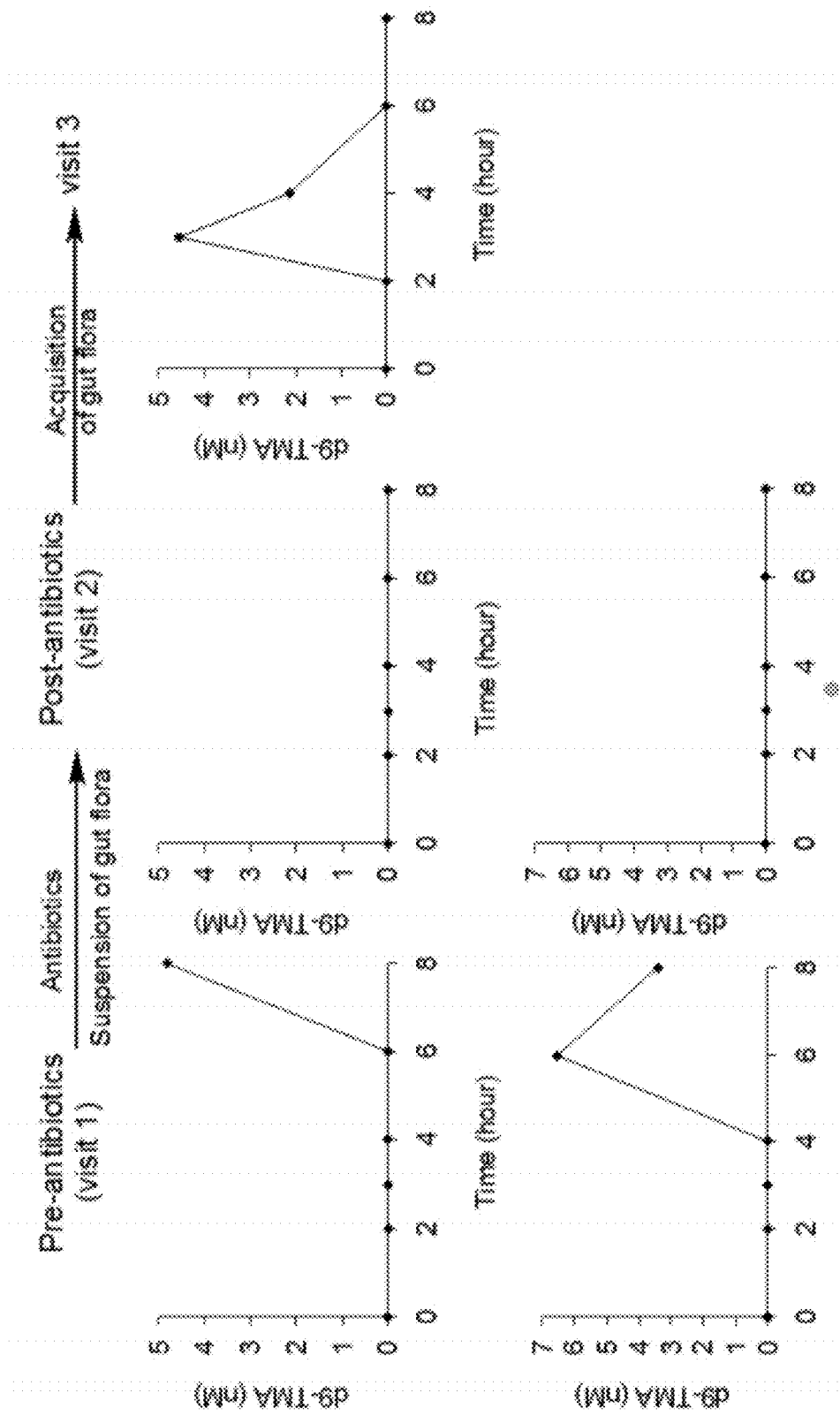
FIG. 11 shows results from Example 9 demonstrating that TMA is generated from ingested phosphatidylcholine (PC, timethyl amine containing compound) in a gut flora dependent fashion in humans.

Subjects were given 250 mg of d9-(trimethyl)-PC, and then time course of d9-TMA in plasma quantified. Note that following the PC challenge, TMA levels increased at 4-8 hours, but were not observed to increase following suppression of intestinal flora with broad spectrum antibiotics (visit 2 data, see FIG. 11). In the first subject, repeat PC challenge one month later after recollonization of the intestines showed again TMA production from the oral PC tracer. Results are shown in FIG. 11. Collectively, these results show TMA is made from oral PC ingestion, and gut flora has an obligatory role in it's generation. Plasma TMA was quantified by LC/MS/MS of samples immediately after blood draw, acidification of the plasma with 10 mM HCl to lower TMA vapor pressure, and snap freezing in liquid nitrogen and storage at −80 C until time of analysis.

Example 10

This Example provides results demonstrating that TMA is increased in congestive heart failure (CHF) vs. healthy controls. Subjects examined had blood TMA (fresh plasma) and exhaled breath TMA quantified. In both cases, the TMA is quantified by mass spectrometry. The exhaled breath is collected into a mylar bag, and then gas analyses by mass spectrometry is performed.

Figure 12:
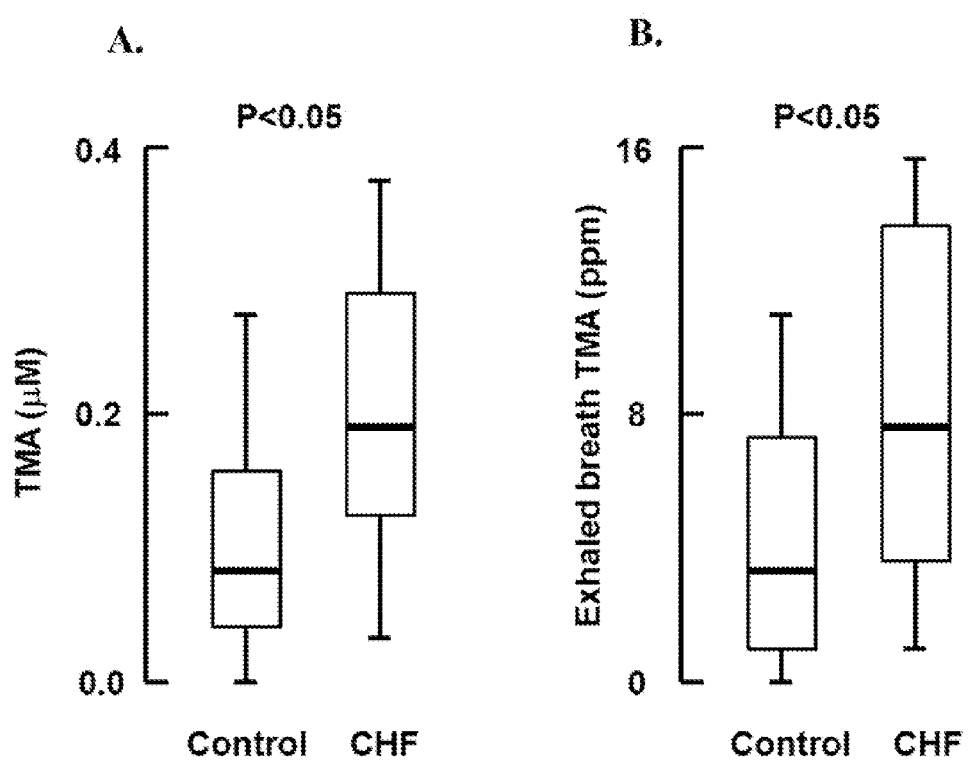
FIG. 12 shows provides results from Example 10 demonstrating that TMA is increased in congestive heart failure (CHF) vs. healthy controls.

Subjects (fasting) with and without CHF were examined for plasma and exhaled breath TMA levels. Plasma TMA was quantified by LC/MS/MS of samples immediately after blood draw, acidification of the plasma with 10 mM HCl to lower TMA vapor pressure, and snap freezing in liquid nitrogen and storage at −80 C until time of analysis. Exhaled breath TMA was quantified by having subjects first brush teeth and wash mouth with water, capture of exhaled breath into Mylar bag, and analysis by mass spectrometry. TMA is increased in both plasma and exhaled breath of subjects with heart failure, a complication of cardiovascular disease. Results are shown in FIG. 12.

Example 11

This Example provides results demonstrating that carnitine and various indicated acylcarnitines are associated with cardiac risk. Sequential subjects (n=2073) undergoing elective cardiac evaluation at the Preventive Cardiology Clinic were consented and enrolled. Fasting blood (EDTA plasma) was collected and analyzed by stable isotope dilution LC/MS/MS analysis for the indicated carnitine molecular species. Data shown, in FIG. 13, are for the odds ratio (per S.D.) for presence of either CAD or CHF in the cohort. These data show that plasma levels of carnitines are associated with increased risk of CAD and CHF. FIG. 13 shows the risk associated with carnitines and both coronary artery disease and congestive heart failure in sequential subjects.

Although only a few exemplary embodiments have been described in detail, those skilled in the art will readily appreciate that many modifications are possible in the exemplary embodiments without materially departing from the novel teachings and advantages of this disclosure. Accordingly, all such modifications and alternative are intended to be included within the scope of the invention as defined in the following claims. Those skilled in the art should also realize that such modifications and equivalent constructions or methods do not depart from the spirit and scope of the present disclosure, and that they may make various changes, substitutions, and alterations herein without departing from the spirit and scope of the present disclosure.

What is claimed is:

1. A method of detecting crotonobetaine in a plasma or serum sample, comprising:
   a) obtaining a biological sample, wherein said biological sample is from a human subject with cardiovascular disease, and wherein said biological sample is a plasma sample, a serum sample, or a urine sample; and
   b) treating said biological sample under conditions such that the concentration of crotonobetaine present in said biological sample is determined by mass spectrometry.

2. The method of claim 1, wherein said biological sample comprises plasma.

3. The method of claim 1, wherein said biological sample is said serum sample.

4. The method of claim 1, wherein said biological sample is said urine sample.

\* \* \* \* \*

UNITED STATES PATENT AND TRADEMARK OFFICE
CERTIFICATE OF CORRECTION

PATENT NO. : 10,241,093 B2
APPLICATION NO. : 13/304806
DATED : March 26, 2019
INVENTOR(S) : Stanley L. Hazen, Zeneng Wang and Bruce Levison It is certified that error appears in the above-identified patent and that said Letters Patent is hereby corrected as shown below:

In the Specification

Add Statement under the title as follows:
STATEMENT OF GOVERNMENTAL INTEREST
This invention was made with government support under HL103866 awarded by the National Institutes of Health. The government has certain rights in the invention.

Signed and Sealed this
Twenty-first Day of March, 2023

Katherine Kelly Vidal
*Director of the United States Patent and Trademark Office*